United States Patent [19]

Mantelle

[11] Patent Number: 5,446,070

[45] Date of Patent: * Aug. 29, 1995

[54] COMPOSITIONS AND METHODS FOR TOPICAL ADMINISTRATION OF PHARMACEUTICALLY ACTIVE AGENTS

[75] Inventor: Juan A. Mantelle, Miami, Fla.

[73] Assignee: Nover Pharmaceuticals, Inc., Miami, Fla.

[*] Notice: The portion of the term of this patent subsequent to Aug. 10, 2010 has been disclaimed.

[21] Appl. No.: 112,330

[22] Filed: Aug. 27, 1993

Related U.S. Application Data

[63] Continuation-in-part of PCT/US92/01730, Feb. 27, 1992, which is a continuation-in-part of Ser. No. 813,196, Dec. 23, 1991, Pat. No. 5,234,957, which is a continuation-in-part of Ser. No. 661,827, Feb. 27, 1991, abandoned.

[51] Int. Cl.$^6$ ............................................. A61K 47/32
[52] U.S. Cl. ................................. 514/772.6; 424/485; 424/486; 424/487; 424/488; 514/781; 514/782
[58] Field of Search ................ 424/435, 443, 447, 449, 424/450, 484, 485, 486, 487, 488; 514/772.6, 818, 947, 781, 782

[56] References Cited

U.S. PATENT DOCUMENTS

| | | | |
|---|---|---|---|
| 2,142,537 | 1/1939 | Tisza | 167/52 |
| 2,277,038 | 3/1942 | Curtis | 167/52 |
| 2,352,691 | 7/1944 | Curtis | 260/472 |
| 2,501,544 | 3/1950 | Shrontz | 128/268 |
| 3,249,109 | 5/1966 | Maeth | 128/268 |
| 3,632,740 | 1/1972 | Robinson | 424/28 |
| 3,640,741 | 2/1972 | Etes | 106/170 |
| 3,814,095 | 6/1974 | Lubens | 128/260 |
| 3,972,995 | 8/1976 | Tsuk | 424/28 |
| 4,302,465 | 11/1981 | Ekenstam | 424/267 |
| 4,307,075 | 12/1981 | Martin | 424/28 |
| 4,466,973 | 8/1984 | Rennie | 424/267 |
| 4,529,601 | 7/1985 | Broberg | 514/626 |
| 4,572,832 | 2/1986 | Kigasawa | 424/19 |
| 4,608,249 | 8/1986 | Otsuka | 424/28 |
| 4,615,697 | 10/1986 | Robinson | 604/890 |
| 4,652,060 | 12/1986 | Broberg | 424/28 |
| 4,659,714 | 4/1987 | Watt-Smith | 514/260 |
| 4,675,009 | 6/1987 | Hymes | 604/304 |
| 4,695,465 | 9/1987 | Kigasawa | 424/19 |
| 4,748,022 | 5/1988 | Busciglio | 424/195 |
| 4,765,983 | 8/1988 | Takayanagi | 424/434 |
| 4,789,667 | 12/1988 | Makino | 514/161 |
| 4,867,970 | 9/1989 | Newsham et al. | 424/435 |
| 4,888,354 | 12/1989 | Chang | 514/424 |
| 4,894,232 | 1/1990 | Reul | 424/439 |
| 4,900,552 | 2/1990 | Sanvordeker | 424/422 |
| 4,900,554 | 2/1990 | Yanagibashi | 424/448 |
| 4,937,078 | 6/1990 | Mezei | 424/450 |
| 4,940,587 | 7/1990 | Jenkins | 424/480 |
| 4,981,875 | 1/1991 | Leusner | 514/774 |
| 5,023,082 | 6/1991 | Friedman | 424/426 |
| 5,234,957 | 8/1993 | Mantelle | 514/772.6 |

FOREIGN PATENT DOCUMENTS

| | | |
|---|---|---|
| 0002425 | 6/1979 | European Pat. Off. . |
| 0139127 | 5/1985 | European Pat. Off. . |
| 0159168 | 10/1985 | European Pat. Off. . |
| 250187 | 6/1987 | European Pat. Off. . |
| 0331392 | 2/1989 | European Pat. Off. . |
| 363224 | 10/1989 | European Pat. Off. . |
| 217989 | 3/1983 | Germany . |
| 52460 | 11/1966 | Luxembourg . |
| 352239 | 12/1972 | Sweden . |
| 1360820 | 7/1974 | United Kingdom . |
| 89/10740 | 11/1989 | WIPO . |

OTHER PUBLICATIONS

J. F. Butterworth, et al., "Molecular Mechanisms of Local Anesthesia: A Review", Anesthesiology 72:711–754, 1990. Pertinent pp. 720–721.

Primary Examiner—Thurman K. Page
Assistant Examiner—Carlos Azpuru
Attorney, Agent, or Firm—Foley & Lardner

[57] ABSTRACT

Compositions for topical application comprising a therapeutically effective amount of a pharmaceutical agent(s), a pharmaceutically acceptable carrier, and a solvent for the pharmaceutical agent(s) in the carrier and methods of administering the pharmaceutical agents to a mammal are disclosed.

45 Claims, No Drawings

COMPOSITIONS AND METHODS FOR TOPICAL ADMINISTRATION OF PHARMACEUTICALLY ACTIVE AGENTS

CROSS-REFERENCE TO RELATED APPLICATIONS

This application is a continuation-in-part of PCT/US92/01730, filed Feb. 27, 1992, which is a continuation-in-part application of U.S. patent application Ser. No. 07/813,196, filed Dec. 23, 1991, now issued as U.S. Pat. No. 5,234,957, which is a continuation-in-part of U.S. patent application Ser. No. 07/661,827 filed Feb. 27, 1991 and now abandoned, all of which applications are hereby incorporated by reference.

BACKGROUND OF THE INVENTION

1. Field of the Invention

The present invention relates to compositions and methods for the topical administration of pharmaceutically active agents to a mammal in need thereof. More particularly, the present invention relates to anesthesia and local anesthetic agents for topical administration. Still more particularly, the invention relates to a method for the topical administration of an anesthetic agent or a combination of anesthetic agents to prevent or ameliorate pain.

There is no limitation on the type of pharmaceutical agent that can be used in the present invention, provided that it can be absorbed topically, typically percutaneously. Thus, the pharmaceutical agent includes both drugs that are topically applied for local effects and those which can be administered topically for systemic effects.

2. Description of Background Art

Anesthetic agents are pharmacologically active agents that block nerve conduction when applied in therapeutically effective amounts. They can be used for local or systemic application. Anesthetic agents have been used extensively in the medical field to obtain topical anesthesia. The term "topical" or "topically" is used here in its coventional sense as referring to a spot, which can be in or on any part of the body, including but not limited to the epidermis, any other dermis, or any other body tissue. Topical administration or application means the direct contact of the anesthetic with tissue, such as skin or membrane, particularly the oral or buccal mucosa. Topical administration also includes application to hardened tissue such as teeth and appendages of the skin such as nails and hair. Previous methods of applying topical anesthetic agents to the skin or mucosa have used "non-finite" or liquid or semi-liquid carriers such as gels, lotions, emulsions, creams, plasters, or ointments, or "finite" carriers, non-spreading substances which retain their form, e.g. patches, dressings and bandages.

Local anesthetics generally are esters or amides of benzoic acid derivatives, administered either as the free base or the acid-addition salt. Free bases tend to be irritating at high concentrations. Acid-addition salts have low skin permeability.

To be effective, a topical, local anesthetic should contain sufficient concentration of the active agent to produce an anesthetic effect, it should penetrate the tissue such as intact skin or mucosa sufficiently to deliver a therapeutic dose, and it should exhibit rapid onset of anesthetic action and have a prolonged anesthetic effect. In achieving the foregoing, it is often desirable to have the anesthetic agent present in a high concentration to effect a rapid onset and, additionally or alternatively, in excess of the amount that can be immediately absorbed through the dermis at the site of application, so as to prolong anesthesia. On the other hand, the presence of the anesthetic agent primarily in crystalline form may irritate sensitive tissues such as mucosal tissues. This is particularly true with regard to lidocaine.

A number of references disclose local anesthetic compositions. For instance, Swedish Patent Publication No. 352,239 published Dec. 27, 1972 in the name of S. G. Davis et al., assigned to Astra Pharmaceutical Products, Inc., and based on Swedish patent application No. 17744/70 filed Dec. 30, 1970, discloses a local anesthetic film containing up to 50% lidocaine in crystallized, microdispersed form. In its final form, this composition lacks a solvent for the anesthetic agent. The preparation is prepared by adding a solution of lidocaine in an organic solvent or an acid addition salt in water, under heat and agitation, to a solution or suspension of a film-forming material, namely carboxymethyl cellulose, polyvinyl alcohol, or a mixture of polyvinyl alcohol and polyvinyl pyrrolidone in water, followed by heating to remove any solvent present.

U.S. Pat. No. 4,937,078 to Mezei, et al. describes a liposome encapsulated local anesthetic or analgesic agent that is said to provide, when applied to the skin or mucous membrane, greater local anesthesia and analgesia than the same agents incorporated in conventional vehicles such as ointments, creams, or lotions. These liposomal films are preferably applied under occlusion.

U.S. Pat. Nos. 4,572,832 and 4,695,465 to Kigasawa and 3,249,109 to Maeth all describe the use of water soluble protein based systems which incorporate anesthetics, and which also contain a tackifier and a polyhydric alcohol solvent. In the compositions of these references, the water soluble protein gives the base its consistency and bulk and serves as an essential vehicle for the incorporation of medicaments and therapeutic agents.

U.S. Pat. No. 4,894,232 to Reül, et al. discloses a base for mucosal or denture adhesive pastes and a process for the preparation thereof. Lidocaine is one possible therapeutic agent suitable for this paste.

U.S. Pat. No. 3,814,095 to Lubens describes an absorbent pad for topical application of an anesthetic agent and having a peripheral adhesive.

It is also known to combine two local anesthetic free bases with different melting points. By mixing the two anesthetic bases, an eutectic mixture has been reported that is liquid at room temperature, making it possible to attain higher concentrations of the active bases.

U.S. Pat. No. 4,888,354 by Chang relates to a combination of the free base and an acid addition salt of a variety of drugs, typically in a liquid carrier, to increase skin penetration rates. Anesthetics, along with a list of other suitable drugs are mentioned. This reference specifically teaches that base and acid-addition forms of the same drug be used in carrier.

U.S. Pat. No. 2,352,691 to Curtis teaches the use of salicylate salts of alkamine esters of amino benzoic acid to enhance the water solubility of anesthetic agents. The salt form predominates over any base form. In one example, this reference discloses a solution of procaine acetyl salicylate containing insoluble anesthetics such as benzocaine, butesin, orthoform, or their salts, in certain glycols which are combined with a volatile solvent, and then used to saturate gauze bandages or other suitable fabrics.

U.S. Pat. No. 2,142,537 to Tisza describes an ointment containing isoamylhydrocupreine in combination with a quick acting local anesthetic to overcome the undesirable irritation caused by the prolonged acting anesthetic isoamylhydrocupreine or its salts. The preparation of Tisza combines short and long acting anesthetic agents. However, such preparation is not provided in a convenient form for topical administration, nor does it appear to contain a high concentration of finely-dispersed drug.

U.S. Pat. No. 4,900,552 by Sanvordeker et al. discloses a trilaminate film suitable for prolonged and sustained delivery of an active ingredient in a buccal cavity. Specifically a hydratable mucoadhesive base layer, a non-adhesive reservoir layer and a water-impermeable carrier film sandwiched between and bonded to the base layer and the reservoir layer form the trilaminate film. This reference generally describes and claims the addition of an active ingredient to the non-adhesive reservoir layer.

U.S. Pat. No. 2,277,038 to Curtis relates to preparations containing a mixture of two or more anesthetic agent salts having different pH values in solution, whereby the pH value of the combined mixture in solution may be adjusted to obtain a higher degree of stability of the solution, and at relatively higher pH, a more rapid onset of anesthetic action. The anesthetic agents in Curtis are not in highly dispersed form and are used in a liquid-soaked fabric.

Procaine salts of different drugs, namely procaine penicillin G, given by intramuscular injection are also known to prolong the antimicrobial action of the antibiotic.

Commonly, prolongation of anesthesia with topical anesthetics has been achieved by the addition of vasoconstrictors, such as the catecholamine, epinephrine, which caused constriction of blood vessels. Since catecholamines are not particularly effective when applied topically, such a prolongation is of minimal usefulness for topical anesthetics. The primary drawbacks of this approach are the potential adverse side effects of catecholamines, and the prolongation itself.

Although many local anesthetic compositions have been proposed, it has been discovered that the incorporation of one or more anesthetic agents in a solvent for the anesthetic agent into a flexible, finite, pharmaceutically acceptable carrier, permits an exceptionally high loading of anesthetic agent in the carrier, permitting more rapid delivery of the anesthetic agent to the tissue such as the dermal membrane without substantive crystallization of the anesthetic agent which can limit absorption by the skin and which can cause irritation of the skin or other dermal membrane or tissue.

It has surprisingly been found that concentrations of substantially dissolved anesthetic agent as high as 50% by weight can be achieved in a system in which the adhesion of the adhesive carrier is not hindered. Prolongation of anesthesia can thus be achieved by increasing the amount of time the composition is applied, without detrimental irritation. The compositions of the present invention are in convenient form for topical application of the anesthetic agents, thereby enabling such anesthetics to penetrate the dermis, for example, intact skin or a mucous membrane. Moreover, the anesthetic action is highly localized. Because the drug is substantially microdispersed in the carrier, it is more readily available for permeation into the tissue, e.g. the skin or dermal membrane.

It still further has surprisingly been found that the use of two different local anesthetic agents, the first in base form and the second in salt form, in a pharmaceutically acceptable carrier in a finite or non-finite form, including a non-aqueous solvent for the anesthetic agents, permits the attainment of high anesthetic agent concentrations in the final product, for example of up to 50% by weight in microdispersed form, without crystallization of the anesthetic agents which can cause irritation of the skin or other dermal membrane or other tissue.

Thus, in one embodiment, the present invention is in convenient form for topical application of the anesthetic agents, thereby enabling such anesthetics to penetrate tissue such as intact skin, skin appendages or mucous membranes and have a highly localized effect. Furthermore, the combination of the salt and base forms, advantageously results in rapid onset of anesthetic action with prolonged anesthetic effect.

SUMMARY OF THE INVENTION

The invention relates to a flexible, finite, bioadhesive composition for topical application comprising:
  (a) a therapeutically effective amount of at least one pharmaceutically active agent which is in solid form at ambient temperatures and pressures;
  (b) a pharmaceutically acceptable solvent for the pharmaceutically active agent, in an amount from about 5 to about 70 weight percent based on the weight of the whole composition, the solvent including about 5 to about 50 weight percent of a plasticizer;
  (c) in admixture with the pharmaceutically active agent in the solvent, a pharmaceutically acceptable polysaccharide bioadhesive carrier in an amount from about 20 to about 50 weight percent based on the weight of the whole composition;
wherein the composition is substantially free of water, substantially water insoluble and is a bioadhesive; and wherein the pharmaceutically active agent is present in non-crystallized form in the composition.

The invention further relates to a composition for topical application comprising:
  (a) a therapeutically effective amount of a first local anesthetic agent in base form;
  (b) a therapeutically effective amount of a different, second local anesthetic agent in non-salicylate acid-addition salt form; and
  (c) in an admixture with the anesthetic agents, a pharmaceutically acceptable carrier
wherein the anesthetic agents comprise about 1 to about 50% by weight of the total composition.

The invention further relates to a composition for topical application comprising:
  (a) a therapeutically effective amount of a first local anesthetic agent in base form;
  (b) a therapeutically effective amount of a different, second local anesthetic agent in acid-addition salt form; and
  (c) in an admixture with the anesthetic agents, a pharmaceutically acceptable carrier which is substantially water free;
wherein the anesthetic agents comprise about 1 to about 50% by weight of the total composition and wherein the amount by weight of the base for an anesthetic agent is equal to or greater than the amount by weight of the salt form.

These compositions may further comprise a backing material which conforms to the size and shape of a single dosage of the composition.

This invention also relates to a method of administering the foregoing compositions.

The invention relates to method of administering one or more pharmaceutically active agents in a bioadhesive to a subject comprising the steps of:

(a) providing a flexible, finite, bioadhesive composition for topical application comprising a therapeutically effective amount of at least one pharmaceutically active agent which is in solid form at ambient temperatures and pressures;

a pharmaceutically acceptable solvent for the pharmaceutically active agent, in an amount from about 5 to about 70 weight percent based on the weight of the whole composition, the solvent including about 5 to about 50 weight percent of a plasticizer;

in admixture with the pharmaceutically active agent in the solvent, a pharmaceutically acceptable polysaccharide bioadhesive carrier in an amount from about 20 to about 50 weight percent based on the weight of the whole composition;

wherein the composition is substantially free of water, substantially water insoluble and is a bioadhesive; and wherein the pharmaceutically active agent is present in non-crystallized form in the composition; and (b) contacting an area of skin or mucous membrane with the composition to administer the pharmaceutically active agent.

The invention further relates to a method of administering a pharmaceutically acceptable composition to a subject, comprising the steps of:

(a) providing a composition comprising a therapeutically effective amount of a first local anesthetic agent in base form; a therapeutically effective amount of a different, second local anesthetic agent in a non-salicylate acid-addition salt form; and in an admixture with the anesthetic agents, a pharmaceutically acceptable carrier;

wherein the anesthetic agents comprise about 1 to about 50% by weight of the total composition; and (b) contacting an area of tissue, such as skin or mucous membrane, with the composition to administer the local anesthetics.

The invention further relates to a method of administering a pharmaceutically acceptable composition to a subject, comprising the steps of:

(a) providing a composition comprising a therapeutically effective amount of a first local anesthetic agent in base form; a therapeutically effective amount of a different, second local anesthetic agent in an acid-addition salt form; and in an admixture with the anesthetic agents, a pharmaceutically acceptable carrier which is substantially free of water wherein the anesthetic agents comprise about 1 to about 50% by weight of the total composition; and (b) contacting an area of tissue, such as skin or mucous membrane, with the composition to administer the local anesthetics.

DETAILED DESCRIPTION OF THE INVENTION

This invention provides a composition which when administered topically, for example to an area of the skin, skin appendage, teeth or mucosa, delivers a pharmaceutical agent or a combination of agents to produce a local or systemic effect over a prolonged period of time.

In accordance with one embodiment of the present invention, a pharmaceutically acive agent and a plasticizer for the adhesive are in admixture with a pharmaceutically acceptable adhesive, which is preferably a bioadhesive, and more preferably a polysaccharide bioadhesive, is provided in a finite, flexible form for topical application to the skin or dermal membrane of a mammal. Preferably, the pharmaceutically active agent is in solid form at ambient temperatures and pressures.

In accordance with a further embodiment of the present invention, a combination of local anesthetic agents, a solvent for the anesthetic agents and a finite or non-finite, fluid or flexible, pharmaceutically acceptable carrier is provided for topical application to a tissue, for example the skin or mucosa of a mammal.

The anesthetic agents of this invention are those known, or of a type known, in the art. The local anesthetic bases encompassed by this invention are weak organic bases which are lipophilic in nature and thus poorly soluble in water. However, these bases will react with organic or inorganic acids to form acidic, water soluble acid addition salts. Thus, the term "base" as used herein means the un-ionized form of the anesthetic that can furnish an electron pair to form a covalent bond. The term "acid" as used herein is a substance that can take up an electron pair to form a covalent bond. The term "salt" as used herein means the form produced by a base, for example an anesthetic base, upon its reaction with an organic or inorganic acid.

The base form and the salt form of the anesthetic agent incorporated in the present combination composition must be different anesthetic agents to achieve maximum duration of the combined anesthetic effect. By the term "different" is meant that the salt form in any combination is not a salt of the base form used in the given combination.

Local anesthetic agents suitable for use in the practice of this invention include amides and esters. Examples of the amides are lidocaine, prilocaine, mepivacaine, bupivacaine, dibucaine and etidocaine. Esters include procaine, tetracaine, propoxycaine, chloroprocaine, benzocaine, butamben picrate, cocaine, hexylcaine, piperocaine, oxyprocaine and proparacaine. Other suitable local anesthetics for use in the practice of this invention include cyclomethycaine, dimethisoquin, ketocaine, diperodon, dyclonine and pramoxine, all typically administered in the form of the acid addition hydrochloride or sulfate salts.

The acid-addition salts of the present invention are any non-toxic, pharmaceutically acceptable organic or inorganic salts which in certain embodiments are non-salicylate. Typical inorganic salts are the hydrogen halides, especially the hydrochlorides, carbonates, borates, phosphates, sulfates, hydrogen sulfates, hydrobromides, nitrates, sulfides, and arsenates. Typical organic salts are salts of mono- and polycarboxylic acids such as the citrate, tartrate, malate, cinnamate, oxalate, formate, succinate and phthalates. The term "non-salicylate" used herein means that in certain embodiments, the acid addition salts do not include salts of esters of salicylic acid and its analogs such as aspririn.

The solvents for the finite and non-finite forms of the anesthetic agents are non-toxic, pharmaceutically acceptable substances, preferably liquids, which do not substantially negatively affect the adhesion properties or solubility of the system. The solvent is preferably a polyhydric alcohol or combination of polyhydric alcohols. The term polyhydric alcohol means any organic polyalcohol and includes dipropylene glycol, propylene glycol, polyethylene glycol, glycerin, butylene glycol, hexylene glycol, polyoxyethylene, polypropylene glycol, sorbitol, ethylene glycol, and the like. Other suitable solvents include fatty acids such as oleic acid, linoleic acid, capric acid and the like, as well as fatty esters or alcohols. Further suitable solvents include other non-toxic, non-volatile solvents commonly used in dermal or transdermal compositions for dissolving like compounds.

The above mentioned polyhydric alcohols may include those having 2 to 6 alcoholic hydroxyl groups. Such polyhydric alcohols include glycols, triols and polyols having 4 to 6 alcoholic hydroxyl groups. Typical of said glycols are glycols containing 2 to 6 carbon atoms, e.g. ethylene glycol, propylene glycol, butylene glycol, polyethylene glycol (average molecular weight about 200–8,000, preferably about 200 to 6,000), etc. Examples of said triols include glycerin, trimethylolpropane, etc. Said polyols are exemplified by sorbitol (sorbit), polyvinylpyrrolidone, etc. These polyhydric alcohols may be used either singly or in combination (preferably, of two or three). Thus, for example, glycerin alone or a mixture of glycerin and butylene glycol is employed.

Among those polyhydric alcohols, those which satisfy the requirements relevant to the adjustment and maintenance of softness of the external surface of the invention, the compatibility or co-dispersibility with the other components, and provide a proper consistency of the composition, may be freely used. Those which are low in volatility are generally preferred and, in this regard, dipropylene glycol, glycerin, propylene glycol, butylene glycol, and sorbitol are appropriate solvents, according to the invention.

Although the exact amount of the polyhydric alcohols in the composition depends on the nature of other components, and therefore cannot be stated in general terms, the proportion may range from about 5 to about 70 or even 90 weight percent based on the whole composition, and depending on the amount of other ingredients.

In one embodiment, the solvent is in an amount from about 20 to 53 weight percent based on the weight of the whole composition. The solvent includes from about 5% to about 50%, and more preferably about 10% to 30% of a solvent known to plasticize the bioadhesive carrier. A particularly useful plasticizer is glycerine.

The high concentrations of microdispersed anesthetic agent of this invention are achieved typically by mixing the anesthetic agents with the solvent, preferably at an elevated temperature, for example about 70° to 100° C., to obtain a mixture, preferably a solution, of the anesthetic agents which is then added to the pharmaceutically acceptable carrier.

The term "microdispersed" is intended to mean that in the solvent, and subsequently the carrier, there is an intimate dispersion of the pharmaceutically active agent at the molecular or ionic level, such that crystals of the pharmaceutically active agent cannot be detected using a microscope having a magnification of 25X. As such, the pharmaceutically active agent is in "non-crystallized" form when in the compositions of the present invention.

Preferably the pharmaceutically active agent is substantially dissolved in the solvent so that when mixed with the finite adhesive or non-finite fluid carrier, the agent is microdispersed in the composition.

Solvent selection for the combination of anesthetic agents depends on the form of the anesthetic agent, namely whether it is in free base form or acid-addition salt form. Solvents for the salt form of anesthetic agent are polar organic solvents. Polar organic solvents are preferably polyhydric alcohols, as discussed above. Various other solvents suitable for either the base or acid-addition form of the anesthetic agent are those solvents known to dissolve either or both of these two types of forms including cyclic ketones such as 2-pyrrolidone; N-(2-hydroxyethyl) pyrrolidone, N-methylpyrrolidone, 1-dodecylazacycloheptan2-one and other n-substituted alkyl-azacycloalkyl-2-ones (azones) dimethylformadide, and dimethylsulfoxide. Other suitable solvents for the free base form of the anesthetic agent are cell envelope disordering compounds known to be useful in topical pharmaceutical preparations, which compounds are thought to assist in skin penetration by disordering the lipid structure of the stratum corneum cell-envelopes. Some of these compounds are generally encompassed by the formula:

$$R-X$$

wherein R is a straight-chain alkyl of about 7 to 16 carbon atoms, a non-terminal alkenyl of about 7 to 22 carbon atoms, or a branched-chain alkyl of from about 13 to 22 carbon atoms, and X is $-OH$, $-COOCH_3$, $-COOC_2H_5$, $-OCOCH_3$, $-SOCH_3$, $-P(CH_3)_2O$, $-COOCH_2H_4OC_2H_4OH$, $-COOCH(CHOH)_4C-H_2OH$, $-COOCH_2CHOHCH_3$, $-COOCH_2CH(OR'')CH_2OR''$, $-(OCH_2CH_2)_mOH$, $-COOR'$, or $-CONR'_2$ where R; is $-H$, $-CH_3$, $-C_2H_5$, $-C_3H_7$ OR $-C_2H_4OH$; R'' is $-H$, or a non-terminal alkenyl of about 7 to 22 carbon atoms; and m is a positive integer from 2 to 6; provided that when R'' is an alkenyl and X is $-OH$ or $-COOH$, at least one double bond is in the cis-configuration.

It has been discovered that high concentrations of a combination of microdispersed anesthetic agents, namely up to 50% by weight of the optionally finite, flexible composition, require the use of a solvent as herein described. In one embodiment of the invention, the anesthetic agent(s) is in an amount of from 10 to 40 weight percent based on the weight of the total composition. Omission of the solvent in the procedure of Example 1 below yields a product filled with crystals or a crystalline mass.

In particularly preferred embodiments of this invention, the free base local anesthetic agent is selected from the group comprising lidocaine, procaine, propoxycaine, mepivacaine, prilocaine, dyclonine, pramoxine, benzocaine and chloroprocaine. The salt form is preferably one selected from the group comprising prilocaine, tetracaine, bupivacaine, dyclonine, dibucaine, etidocaine and lidocaine salts. The aforementioned bases and salts can be used alone or in combination with other anesthetic bases and salts as needed to achieve therapeutically effective levels when administered transdermally, or through other topical route.

The term "therapeutically effective amount" is intended to mean the amount of drug sufficient to produce an anesthetic effect when applied topically. These amounts are known in the art or may be determined by methods known in the art, and typically range from about 1 to 20,000 mg per human adult and preferably about 10 to 10,000 mg and most preferably range from about 20 to 5,000 mg of the anesthetic agent per application, depending upon the anesthetic agents chosen, and whether the tissue, such as the skin or mucous membrane is the site of action. The only upper limit on the amount of anesthetic in the composition is that the preparation is substantially free of crystals of anesthetic agent and the amount of solvent used is not sufficient to undesirably affect the adhesive properties of the finite composition. Thus, the single ingredient anesthetic agent contains a therapeutically effective amount of anesthetic agent within the foregoing range.

The concentration as well as the quantity of anesthetic per unit area, namely per square or cubic centimeter can be varied independently in order to achieve the desired effect. Higher concentrations of anesthetic base contained in a dosage form of decreased thickness will result in an anesthetic with fast onset and short duration. High concentrations of the anesthetic base contained in a dosage form of increased thickness (higher mg of anesthetic per square or cubic centimeter) will result in potent anesthesia with fast onset and long duration. Low concentrations of the anesthetic base in a dosage form of decreased thickness will result in mild anesthesia with longer onset and short duration. Low concentrations of the anesthetic base contained in a dosage form of increased thickness will have mild anesthesia with longer onset and longer duration. As shown in the above explanation, the ability to vary the concentration of anesthetic from very low (about 1%) to high (40% or higher) of the total composition, when combined with the ability to coat thin (about 0.001 inches) or thick (about 0.500 or more inches) enables the practitioner of the invention to vary the dosage of the system as needed for particular anatomical sites of interest.

As a general rule, in the case of a given tissue, e.g. the mucosal application, the anesthetic drug selected, the concentration and thickness and the duration of the application is determined based upon the anesthetic's ability to penetrate the tissue, for example mucosa, and to be at peak effectiveness within about 2 to 30 minutes. The duration of the effect of the anesthetic on the tissue, for example the oral mucosa, should range between about 2 to 240 minutes, depending on the anesthetic agent selected, the concentration of the anesthetic and the thickness of application. Longer or shorter durations can also be selected dependent on need, as will be apparent to one skilled in the art.

The ratio of the free base form to the salt form in the composition of this invention will depend on several factors, namely: (1) the identity of the salt and base used; (2) the desired duration of action; and (3) the desired rapidity of anesthetic effect. As a general rule in the case of mucosal application, the ratios of base to salt are such that the free base form preferably should penetrate the mucosa and be at its peak effectiveness within about a 2 to 30 minute period, whereas, the salt form should preferably penetrate the mucosa and be at its peak effectiveness within a period of about 10 to 75 minutes. The duration of the effect of these on the oral mucosa will range between about 2 to 240 minutes depending on the base/salt combination selected and the length of application time. In practice to achieve this effect, the amount by weight base form will be in excess of the amount by weight of the salt form.

The term "onset of anesthesia" is intended to mean the time to peak effect on the individual nerves. Onset of anesthesia principally depends upon the lipid solubility, molecular size, and quantity of available, un-ionized form of the local anesthetic. Thus, anesthetics with a high lipid solubility or a low $pK_a$, or both, have a more rapid onset of anesthesia.

The term "duration of anesthesia" as used herein means the period of time during which the local anesthetic measurably blocks nerve conduction. The foregoing depends upon all of the factors listed for onset of anesthesia, as well as on the extent of protein binding of the anesthetic agent.

The anesthetic agent free base can penetrate intact skin to a limited degree, and will more rapidly penetrate the skin if the keratin layers are abraded. In the case of the oral mucosa, the anesthetic base will penetrate much more readily due to the different keratin composition and the resulting difference in the hydrophilicity as compared to the stratum corneum of intact skin.

As a general rule, the salt forms of the aforementioned anesthetics do not appreciably penetrate intact skin, but the un-ionized base form do penetrate to a limited degree. Both forms, salt and base, will penetrate abraded keratin layers. The salt as well as the base will penetrate, to a differing degree, the buccal mucosa due to the buccal mucosa's hydrophilicity, as compared to the stratum corneum of intact skin. Generally, the higher the lipid content of the mucosal membrane, the more rapidly the base form of the anesthetic agent will be absorbed. Therefore, when the composition is used for application to oral or buccal mucosa, the different lipid contents of the gum (gingiva) and the alveolar mucosa must be kept in mind in order to obtain the optimal penetration rate.

Although applicants do not intend to be bound by any theory or proposed mechanism of operation, it is believed that the base which is lipid soluble has a rapid onset of anesthesia since it enters the lipo-protein nerve membrane preventing the depolarization and ion exchange involved in stimulus conduction. On the other hand, the salt which is not lipid soluble, penetrates to the lipo-protein nerve membrane only after the buffering capacity of the skin or mucosal tissue converts the salt to the base, the final result being a delayed onset of anesthesia.

The salts of this invention are selected on the basis of onset of anesthesia and duration of anesthesia. Adjusting the ratio of base to salt affects the relative onset as well as the duration of anesthetic action. The greater the amount of anesthetic agent having a rapid onset of action, the shorter the onset of anesthesia. Similarly, the greater the amount of the anesthetic agent having a prolonged duration of anesthesia, the more prolonged the duration of anesthesia. More than two anesthetic agents may be used to have a broader spectrum of activity. Moreover, the composition can include other drugs used concomitantly.

Generally, the concentration of solubilized pharmaceutically active agent can range, on a weight basis, between about 1 and about 50%, preferably between 2.5 and 40% and more preferably between 5 and 30% of the total weight of the composition. In a preferred embodiment of the invention, the concentration of the dissolved drug is between 5% and 20% by weight of the total composition. The base used in the preferred embodiment for a single ingredient preparation is lidocaine.

Generally, for the combination of anesthetics, the ratio by weight of base to salt is about 90:10 to about 60:40, preferably about 75:25 to about 60:40, and more preferably about 70:30 to about 60:40. For other salts, the ratios are comparable based on relative molar amounts. Generally, the ratio by weight of base to salt is more than 1:1. In a preferred embodiment of the invention, the ratio is about 2:1 base to salt, respectively. The base used in the preferred embodiment is lidocaine and the preferred salt is a salt of prilocaine, bupivacaine, dyclonine, mepivacaine, or tetracaine, preferably the hydrochloride salt.

Table 1 below summarizes the peak and duration of action of selected local anesthetics based primarily on application to skin or mucous membranes:

TABLE 1

| Local Anesthetic | Minimum Adult Dose | Maximum Adult Dose (mg) | Peak Effect (minutes) | Duration of Effect (minutes) |
|---|---|---|---|---|
| Dibucaine | | 25 | <15 | 120–240 |
| Lidocaine | | 750 | 2–5 | 30–60 |
| Benzocaine | | 5000 | 1 | 30–60 |
| Cocaine | | 50 | 2–5 | 30–120 |
| Tetracaine | | 50 | 3–8 | 30–60 |
| Dyclonine | | 100 | <10 | <60 |
| Pramoxine | | 200 | 3–5 | NA |

NA: Not Available.
Source: Drug Facts and Comparisons, 1990 edition, J.B. Lippincott Company, St. Louis, MO. Page 601.

In general, the relative speed of onset of anesthesia and duration of anesthesia for any given form of anesthetic agent is available in the literature or can be calculated by standard tests.

Onset time, as well as duration of anesthesia, will vary from individual to individual as well as on the basis of the site of application. When applying the composition to highly keratinized dermal tissues, the onset of anesthesia may take as long as 2 to 4 hours.

The composition of this invention can be manufactured by numerous methods known in the art which permit the achievement of a microdispersed anesthetic agent, including extruding, molding, solvent casting, coating, and all other methods which employ a solvent to disperse the drug in a finite or non-finite carrier.

In one embodiment of the invention, the composition comprises a combination of a first anesthetic agent in the form of a base and a second anesthetic agent in the form of an acid-addition salt. In this embodiment, the term "pharmaceutically acceptable carrier" is intended to be any suitable finite or non-finite carrier including liquids, semi-liquids or solid carriers, such as a bioadhesive. Thus, the active agents may be admixed with a non-adhesive tape or other finite carrier or a carrier such as a cream, gel, emulsion, lotion, salve, paste, plaster, ointment, spray-solution, or any other "non-finite" carrier known in the art of pharmaceutical delivery. For example, the base of a non-finite carrier may be fatty oils, lanolin, vaseline, paraffins, glycols, higher fatty acids and higher alcohols.

Contrary to the typical method for manufacturing a drug in a solvent containing adhesive, the adhesive composition of this invention contains a non-volatile solvent. Thus the composition is either not dried to prevent removal of the solvent from the adhesive or a solvent is used at least part of which is not substantially evaporated during the conditions of manufacture. The composition in question can then be applied to a flexible backing or a combination of backings which will serve to define the size and shape of a single dosage of the composition. Such backing may be a three dimensional material such as paper, a non-woven fabric or a natural or synthetic polymer substance. Methods of coating backings are well-known in the art and include techniques involving Mayer rod, gravure, and knife-over roll. Further processing of backings may involve the use of converting equipment for die cutting.

The finished dosage form will be substantially occlusive to water permeation in in-vivo.

For example, in one embodiment, the anesthetic agents are dissolved in a solvent, preferably a polyhydric alcohol, and then the resulting mixture is added to an adhesive prior to being placed onto the flexible form or backing. In another embodiment, the resulting mixture is an cream, gel, emulsion, lotion, salve, plaster, paste, ointment, spray-solution or other "non-finite" composition. The final form in which the composition of the invention will be applied depends upon the anatomical site of application and ease of access.

The phrase "flexible, finite, pharmaceutically acceptable carrier" is intended to mean a solid capable of conforming to a surface with which it comes into contact and which is capable of maintaining the contact so as to facilitate topical application without any adverse physiological response, and which can be used to establish the compositions herein in their preferred solid form without being appreciably decomposed by aqueous contact during administration to a patient.

An important characteristic of the embodiment of the present invention wherein a bioadhesive carrier is employed, relates to the substantially water-free and water-insoluble nature of the composition. By the term "substantially water-free" is meant that the preparation contains less than about 10% by weight water, and preferably less than 5%, and most preferably less than 3%. In general, it is desirable to avoid the addition of water entirely and to eliminate, as far as possible, the presence of water in the other ingredients of the composition. By the term "substantially water insoluble" is meant that the composition remains "finite" and does not generally detach from the skin, dermal membrane or other tissue at the site of application and under the conditions of regular, intended use for a period of at least 3 hours. The advantages to be derived from the substantially water-free and water-insoluble nature of the compositions of the present invention include achievement of higher concentrations of drug. Another advantage of these compositions is minimization of precipitation of drug, which precipitation affects processing of the composition, affects rate of delivery of the drugs and in certain cases can affect sensitivity of the subject to be treated to the drug.

Suitable adhesive carriers include any of the non-toxic polymers, particularly those of the type used to carry drugs for transdermal delivery including natural or synthetic elastomers, such as polyisobutylene, styrene, butadiene, styrene isoprene block copolymers, acrylics, urethanes, silicones, styrene butadiene copolymers, methyl acrylate copolymers, acrylic acid, polyacrylates, and polysacchrides such as, karaya gum, tragacanth gum, pectin, guar gum, cellulose, and cellulose derivatives such as methyl cellulose, propyl cellulose, cellulose acetate and the like, along with other substances known for use in transdermal preparations capable of forming a solid colloid that can adhere to tissue, used alone or in combination with other suitable carriers. A particularly preferred carrier is a bioadhesive for application to the dermis, preferably the mucosa.

The adhesive can be modified so as to adhere to the skin or mucosal tissue, depending on the intended application site. As stated above, preferred adhesives for application to the skin are bioadhesives.

The term "adhesive" as used herein means a substance, inorganic or organic, natural or synthetic, that is capable of surface attachment to the intended application site.

The term "bioadhesive" as used herein means an adhesive which attaches and preferably strongly attaches to a live or freshly killed biological surface such as skin or mucosal tissue upon hydration. Indeed, to qualify as a bioadhesive, a substance must be capable of maintaining adhesion in moist or wet in in vivo or in vitro environments. The final finite composition of the present invention is "self-adhesive" in that it attaches to the site of interest without the need to reinforce its attachment by way of another adhesive which is applied to a backing.

The strength of adherence can be measured by standard tests for measuring the force, e.g. in dynes per square centimeter, as disclosed in U.S. Pat. No. 4,615,697. Suitable bioadhesives include those prepared from optionally partially esterified polyacrylic acid polymers, including but not limited to, polyacrylic acid polymers lightly crosslinked with a polyalkenyl polyether such as those commercially available from B. F. Goodrich, Cincinnati, Ohio, under the trademarks Carbopol 934, 934P, 940 and 941.

Other suitable bioadhesives include natural or synthetic polysaccharides. The term "polysaccharide" as used herein means a carbohydrate decomposable by hydrolysis into two or more molecules of monosaccharides or their derivatives. Suitable polysaccharides include cellulose derivatives such as methylcellulose, cellulose acetate, carboxymethylcellulose, hydroxyethylcellulose and the like. Other suitable bioadhesives are pectin, a mixture of sulfated sucrose and aluminum hydroxide, hydrophilic polysaccharide gums such as natural plant exudates, including karaya gum, ghatti gum, tragacanth gum, xanthan gum, jaraya gum and the like, as well as seed gums such as guar gum, locust bean gum, psillium seed gum and the like. The term non-finite carrier refers to any liquid or semi liquid known for or suitable for use in pharmaceutical preparations as will be apparent to one skilled in the art.

In addition to the above ingredients, there may also be incorporated other additives selected from among the various pharmaceutically acceptable additives available to those skilled in the art. These additives include binders, stabilizers, preservatives, flavorings and pigments. In a preferred finite form embodiment, the compositions of the present invention also contain a binder such as lecithin which "binds" the other ingredients, thereby enhancing the uniform consistency of the final composition.

The composition is administered in appropriate sizes, typically having a surface area of from about 0.1 to about 200 cm² or conveniently 0.2 to 100 cm². The anesthetic agent is loaded into the composition in as high a concentration as necessary to effect therapy, e.g., in a range from about 0.1 mg/cm² to about 50 or more mg/cm² or 0.1 mg/ml to about 500 or more mg/ml when a non-finite carrier such as an ointment, gel, lotion, cream, paste, plaster, emulsion, or spray-solution is used.

In general, the composition can have the following types and amounts of ingredients:

| Ingredient | Typical Range (% by weight) | Preferred Range (% by weight) | Optimum Range (% by weight) |
|---|---|---|---|
| Finite Form | | | |
| Adhesive | 15 to 60 | 20 to 50 | 20 to 35 |
| Solvent (with plast.) | 2 to 75 | 5 to 70 | 20 to 40 |
| Anesthetic agent (single ingredient) | 1 to 50 | 5 to 40 | 10 to 30 |
| Anesthetic agent (multiple ingredient) | 1 to 50 | 5 to 40 | 10 to 30 |
| Anesthetic base | .7 to 50 | 5 to 40 | 7 to 20 |
| Anesthetic salt | .3 to 25 | 2 to 30 | 3 to 20 |
| Non-finite Form | | | |
| Solvent | 2 to 90 | 5 to 70 | 20 to 40 |
| Anesthetic agent (single ingredient) | 1 to 50 | 5 to 40 | 10 to 30 |
| Anesthetic agent (multiple ingredient) | 1 to 50 | 5 to 40 | 10 to 30 |
| Anesthetic base | .7 to 50 | 5 to 40 | 7 to 20 |
| Anesthetic salt | .3 to 25 | 2 to 30 | 3 to 20 |

In one embodiment, the flexible, finite, bioadhesive composition for topical application comprises:
  a therapeutically effective amount of at least one pharmaceutically active agent which is in solid form at ambient temperatures and pressures;
  a pharmaceutically acceptable solvent for the pharmaceutically active agent, in an amount from about 5 to about 70 weight percent based on the weight of the whole composition, said solvent including about 5 to about 50 weight percent of a plasticizer for the bioadhesive;
  in admixture with the pharmaceutically active agent in the solvent, a pharmacetuically acceptable polysaccharide bioadhesive in an amount from about 20 to about 50 weight percent based on the weight of the whole composition; wherein the composition is substantially water insoluble and self-adhesive; and wherein the pharmaceutically active agent is present in non-crystallized from in the composition.

In another embodiment, the invention relates to a composition and method of administering:
  (a) a therapeutically effective amount of a first local anesthetic agent in base form;
  (b) a therapeutically effective amount of a different, second local anesthetic agent in non-salicylate acid-addition salt form; and
  (c) in an admixture with the anesthetic agents, a pharmaceutically acceptable carrier;
wherein the anesthetic agents comprise about 1 to about 50% by weight of the total composition.

The invention further relates to a composition and method of administering:
  (a) a therapeutically effective amount of a first local anesthetic agent in base form;
  (b) a therapeutically effective amount of a different, second local anesthetic agent in acid-addition salt form; and
  (c) in an admixture with the anesthetic agents, a pharmaceutically acceptable carrier which is substantially free of water;
wherein the anesthetic agents comprise about 1 to about 50% by weight of the total composition and wherein said composition is substantially free of water.

The term "administering" is intended to mean any mode of application to a tissue which results in the physical contact of the composition with an anatomical site in need of anesthesia. The term "subject" is intended to include all warm-blooded mammals, preferably humans.

In one method of the invention wherein a bioadhesvie carrier is employed, the pharmaceutically acceptable solvent is in a preferred amount from about 20 to about 53 weight percent of which the plasticizer represents about 10 to 30 weight percent based on the weight of the whole composition and the bioadhesive carrier is in an amount from about 20 to about 34 weight percent based on the weight of the whole composition. More preferably, the bioadhesive composition of this method is comprised of 20 to 34 weight percent of karaya gum, about 20 to 53 weight percent of at least one glycol, and about 10 to 25 weight percent of lidocaine base and is further comprised of a binder in an amount sufficient to bind the other ingredients.

The following examples will further describe the instant invention, and are used for the purposes of illustration only, and should not be considered as limiting in any way the invention being disclosed herein. Percent (%) as used in these examples refer to percentage of the liquid formulation on a weight to weight basis and temperatures are given in degrees celsius (°C.).

EXAMPLE 1

| Ingredient | % (w/w) |
| --- | --- |
| Adhesive (karaya gum) | 21 |
| Binder (lecithin) | 11 |
| Solvent (propylene glycol) | 7 |
| Solvent (glycerin) | 19 |
| Anesthetic agent base (lidocaine base) | 28 |
| Anesthetic agent salt (prilocaine hydrochloride) | 14 |

The final product is manufactured by first blending the lidocaine base, prilocaine hydrochloride, propylene glycol, lecithin and glycerin at about 70° to 90° C. until all of the drug is dissolved. The solution is then cooled to 20° to 35° C. prior to adding the karaya gum. Once the karaya gum is added, the final composition is applied to a suitable backing material such as a non-woven, polyester film (for example, the film sold under the trademark Sontara 8100, manufactured by DuPont de Nemours, E. I. and Co., Wilmington, Del.) and warmed to about 100° C. to accelerate the formation of the gel into its final, finite form.

EXAMPLE 2

| Ingredient | % (w/w) |
| --- | --- |
| Adhesive (karaya gum) | 30 |
| Solvent (glycerin) | 30 |
| Solvent (propylene glycol) | 39 |
| Anesthetic agent base (lidocaine base) | 0.7 |
| Anesthetic agent salt (prilocaine hydrochloride) | 0.3 |

The procedure set forth in Example 1 is used with appropriate substitutions of quantities to prepare this formulation.

EXAMPLE 3

| Ingredient | % (w/w) |
| --- | --- |
| Adhesive (karaya gum) | 21 |
| Binder (lecithin) | 4 |
| Solvent (propylene glycol) | 3 |
| Solvent (isocetyl alcohol) | 7 |
| Solvent (glycerin) | 26 |
| Anesthetic agent base (lidocaine base) | 26 |
| Anesthetic agent salt (tetracaine hydrochloride) | 13 |

The procedure of Example 1 is used with appropriate substitution of ingredients to prepare this formulation.

EXAMPLE 4

| Ingredient | % (w/w) |
| --- | --- |
| Adhesive (karaya gum) | 27 |
| Solvent (propylene glycol) | 29 |
| Solvent (glycerin) | 4 |
| Anesthetic agent base (lidocaine base) | 28 |
| Anesthetic agent salt (dyclonine hydrochloride) | 12 |

The procedure of Example 1 is used with appropriate substitution of ingredients to prepare this formulation.

EXAMPLE 5

| Ingredient | % (w/w) |
| --- | --- |
| Adhesive (karaya gum) | 26 |
| Binder (lecithin) | 10 |
| Solvent (propylene glycol) | 7 |
| Solvent (butylene glycol) | 17 |
| Solvent (glycerin) | 10 |
| Anesthetic agent base (lidocaine base) | 20 |
| Anesthetic agent salt (dyclonine hydrochloride) | 10 |

The procedure of Example 1 is used with appropriate substitution of ingredients to prepare this formulation,

EXAMPLE 6

| Ingredient | % (w/w) |
| --- | --- |
| Adhesive (karaya gum) | 27 |
| Binder (lecithin) | 12 |
| Solvent (propylene glycol) | 8 |
| Solvent (glycerin) | 13 |
| Anesthetic agent base (lidocaine base) | 27 |
| Anesthetic agent salt (bupivacaine hydrochloride) | 13 |

The procedure of Example 1 is used with appropriate substitution of ingredients to prepare this formulation.

EXAMPLE 7

| Ingredient | % (w/w) |
| --- | --- |
| Adhesive (karaya gum) | 27 |
| Binder (lecithin) | 12 |
| Solvent (propylene glycol) | 8 |
| Solvent (glycerin) | 13 |
| Anesthetic agent base (lidocaine base) | 13 |
| Anesthetic agent salt (bupivacaine hydrochloride) | 27 |

The procedure of Example 1 is used with appropriate substitution of ingredients to prepare this formulation.

EXAMPLE 8

| Ingredient | % (w/w) |
| --- | --- |
| Adhesive (karaya gum) | 21 |
| Binder (lecithin) | 11 |
| Solvent (propylene glycol) | 7 |

-continued

| Ingredient | % (w/w) |
|---|---|
| Solvent (glycerin) | 19 |
| Anesthetic agent base (lidocaine base) | 28 |
| Anesthetic agent salt (mepivacaine hydrochloride) | 14 |

The procedure of Example 1 is used with appropriate substitution of ingredients to prepare this formulation.

EXAMPLE 9

| Ingredient | % (w/w) |
|---|---|
| Adhesive (Carbopol 934P, a polycarboxylic acid sold by B. F. Goodrich Chemical Company) | 20 |
| Solvent (propylene glycol) | 15 |
| Solvent (glycerin) | 20 |
| Anesthetic agent base (lidocaine base) | 30 |
| Anesthetic agent salt (bupivacaine hydrochloride) | 15 |

The procedure of Example 1 is used with appropriate substitution of ingredients to prepare this formulation.

EXAMPLE 10

| Ingredient | % (w/w) |
|---|---|
| Adhesive (karaya gum) | 24 |
| Solvent (propylene glycol) | 3 |
| Adhesive (glycerin) | 14 |
| Solvent (isocetyl alcohol) | 7 |
| Binder (lecithin) | 4 |
| Anesthetic agent base (lidocaine base) | 32 |
| Anesthetic agent salt (tetracaine hydrochloride) | 16 |

The above formulation is prepared by a procedure which is analogous to that set forth in Example 1.

The addition of up to 2% by weight water in this formulation did not result in precipitation of the anesthetic agent(s) prior to addition of the karaya gum. The addition of 3% to 10% water results in increased precipitation, which at 10% water results in a crystalline mass.

EXAMPLE 11

| Ingredient | % (w/w) |
|---|---|
| Adhesive (tragacanth gum) | 24 |
| Adhesive (pectin) | 5 |
| Solvent (propylene glycol) | 12 |
| Solvent (glycerin) | 12 |
| Anesthetic agent base (mepivacaine base) | 35 |
| Anesthetic agent salt (lidocaine hydrochloride) | 12 |

The above formulation is prepared by a procedure analogous to that of Example 1.

EXAMPLE 12

| Ingredient | % (w/w) |
|---|---|
| Bioadhesive (karaya gum) | 33 |
| Binder (lecithin) | 9 |
| Solvent (propylene glycol) | 6 |
| Solvent (dipropylene glycol) | 15 |
| Solvent (glycerin) | 17 |
| Anesthetic agent base (lidocaine base) | 20 |

The final product is manufactured by first blending the lidocaine base, lecithin, propylene glycol, dipropylene glycol and glycerine at about 70° to 90° C. until all of the drug is dissolved. The solution is then chilled to about 20° to 40° C. prior to adding the karaya gum. Once the karaya gum is added, the final composition is applied to a suitable backing material such as a non-woven polyester film (for example the film sold under the trademark Sontata 8100 manufactured by DuPont de Nemours, E. I. and Co., Wilmington, Del.) and warmed at about 708° to 130° C. to accelerate the formation of the gel into its final solid form. This gel can be directly applied to the oral mucosa or overlaid with a skin contact adhesive for skin adhesion.

EXAMPLE 13

| Ingredient | % (w/w) |
|---|---|
| Bioadhesive (karaya gum) | 33 |
| Binder (lecithin) | 5 |
| Solvent (propylene glycol) | 7 |
| Solvent (dipropylene glycol) | 12 |
| Solvent (glycerin) | 33 |
| Anesthetic agent base (lidocaine base) | 10 |

The procedure of Example 12 is used with appropriate substitution of ingredients to prepare this formulation.

EXAMPLE 14

| Ingredient | % (w/w) |
|---|---|
| Bioadhesive (karaya gum) | 35 |
| Binder (lecithin) | 5 |
| Solvent (propylene glycol) | 7 |
| Solvent (dipropylene glycol) | 12 |
| Solvent (glycerin) | 36 |
| Anesthetic agent base (lidocaine base) | 5 |

The procedure of Example 12 is used with appropriate substitution of ingredients to prepare this formulation.

EXAMPLE 15

| Ingredient | % (w/w) |
|---|---|
| Bioadhesive (karaya gum) | 30 |
| Binder (lecithin) | 9 |
| Solvent (propylene glycol) | 6 |
| Solvent (dipropylene glycol) | 15 |
| Solvent (glycerin) | 15 |
| Anesthetic agent base (lidocaine base) | 25 |

The procedure of Example 12 is used with appropriate substitution of ingredients to prepare this formulation.

EXAMPLE 16

| Ingredient | % (w/w) |
|---|---|
| Bioadhesive (karaya gum) | 20 |
| Binder (lecithin) | 9 |
| Solvent (propylene glycol) | 6 |
| Solvent (dipropylene glycol) | 10 |
| Solvent (glycerin) | 10 |
| Solvent (benzyl alcohol) | 5 |
| Anesthetic agent base (lidocaine base) | 40 |

The procedure of Example 12 is used with appropriate substitution of ingredients to prepare this formulation.

EXAMPLE 17

| Ingredient | % (w/w) |
| --- | --- |
| Bioadhesive (karaya gum) | 25 |
| Binder (lecithin) | 8 |
| solvent (isocetyl alcohol) | 5 |
| Solvent (propylene glycol) | 12 |
| Solvent (glycerin) | 10 |
| Anesthetic agent base (prilocaine base) | 40 |

The procedure of Example 12 is used with appropriate substitution of ingredients to prepare this formulation.

EXAMPLE 18

| Ingredient | % (w/w) |
| --- | --- |
| Bioadhesive (karaya gum) | 25 |
| Binder (lecithin) | 4 |
| Solvent (propylene glycol) | 6 |
| Solvent (benzyl alcohol) | 10 |
| Solvent (dipropylene glycol) | 10 |
| Solvent (glycerin) | 5 |
| Anesthetic agent base (tetracaine base) | 40 |

The procedure of Example 12 is used with appropriate substitution of ingredients to prepare this formulation.

EXAMPLE 19

| Ingredient | % (w/w) |
| --- | --- |
| Bioadhesive (karaya gum) | 30 |
| Binder (lecithin) | 8 |
| Solvent (propylene glycol) | 12 |
| Solvent (dipropylene glycol) | 25 |
| Solvent (benzyl alcohol) | 5 |
| Solvent (glycerin) | 10 |
| Anesthetic agent base (dibucaine base) | 10 |

The procedure of Example 12 is used with appropriate substitution of ingredients to prepare this formulation.

EXAMPLE 20

| Ingredient | % (w/w) |
| --- | --- |
| Bioadhesive (karaya gum) | 28 |
| Bioadhesive (Carbopol 934) | 2 |
| Solvent (propylene glycol) | 6 |
| Solvent (dipropylene glycol) | 15 |
| Solvent (glycerin) | 15 |
| Binder (lecithin) | 9 |
| Anesthetic agent base (lidocaine base) | 25 |

The procedure of Example 12 is used with appropriate substitution of ingredients to prepare this formulation. The only difference is that the Carbopol 934 is added to the original blend prior to heating it.

EXAMPLE 21

| Ingredient | % (w/w) |
| --- | --- |
| Bioadhesive (tragacanth gum) | 27 |
| Bioadhesive (pectin) | 6 |
| Binder (lecithin) | 9 |
| Solvent (propylene glycol) | 6 |
| Solvent (dipropylene glycol) | 15 |
| Solvent (glycerin) | 17 |
| Anesthetic agent base (lidocaine base) | 20 |

The procedure of Example 12 is used with the solvents and anesthetic agent base added in the initial step followed later by the adhesives addition.

EXAMPLE 22

| Ingredient | % (w/w) |
| --- | --- |
| Bioadhesive (cellulose acetate) | 27 |
| Solvent (dipropylene glycol) | 43 |
| Anesthetic agent base (prilocaine base) | 20 |

This formulation is prepared according to the procedure which is analogous to the procedure set forth in Example 1.

EXAMPLE 23

| Ingredient | % (w/w) |
| --- | --- |
| Bioadhesive (xanthan gum) | 27 |
| Bioadhesive (pectin) | 6 |
| Binder (lecithin) | 9 |
| Solvent (propylene glycol) | 6 |
| Solvent (dipropylene glycol) | 15 |
| Solvent (glycerin) | 17 |
| Anesthetic agent base (lidocaine base) | 20 |

The procedure of Example 12 is followed with the appropriate substitution of ingredients.

EXAMPLE 24

| Ingredient | % (w/w) |
| --- | --- |
| Drug (miconazole nitrate) | 2 |
| Solvent (Propylene glycol) | 67 |
| Thickener (hydroxymethylcellulose) | 1 |
| Adhesive (karaya gum) | 30 |
| Anesthetic agent base (lidocaine base) | 20 |

This formulation is prepared by dispersing the hydroxymethylcellulose into propylene glycol. Once the hydroxymethylcellulose is dispersed, the drug is added at a temperature between 50° and 80° C. and mixed until dissolved. The sample is then cooled to approximately 20° to 35° C. prior to adding the karaya gum. Once the karaya gum is added, the formulation is applied to a sheet of backing material, then the individual dosage forms are cut to the desirable shape to contain the desired amount of drug.

EXAMPLE 25

| Ingredient | % (w/w) |
| --- | --- |
| Binder (lecithin) | 4 |
| Solvent (propylene glycol) | 26 |
| Solvent (isocetyl alcohol) | 7 |
| Solvent (glycerin) | 14 |
| Anesthetic agent base (lidocaine base) | 32 |
| Anesthetic agent salt (tetracaine HCl) | 16 |
| Thickener (hydroxypropyl cellulose Klucel, HF) | 1 |

The Klucel, HF is dispersed in propylene glycol in order to make a 3% dispersion. In a separate container, the remaining propylene glycol, isocetyl alcohol, lidocaine base, tetracaine HCl, and lecithin are blended at 70°–90° C. This mixture is then allowed to cool prior to blending with the 3% Klucel solution in propylene glycol. Upon mixing the two parts, an ointment results.

EXAMPLE 26

| Ingredient | % (w/w) |
|---|---|
| Binder (lecithin) | 28 |
| Solvent (propylene glycol) | 19 |
| Solvent (glycerin) | 47 |
| Anesthetic agent base (lidocaine base) | 4 |
| Anesthetic agent salt (prilocaine HCl) | 2 |

The lidocaine base, prilocaine HCl, glycerin, propylene glycol and lecithin are blended at 70°–90° C. until the drug is dissolved. The mixture is then allowed to cool down to room temperature under gentle mixing resulting in an ointment.

EXAMPLE 27

| Ingredient | % (w/w) |
|---|---|
| Binder (surfactin) | 2 |
| Thickener (Carbopol 934P) | 2 |
| Solvent (water) | 85 |
| Solvent (propylene glycol) | 5 |
| Anesthetic agent base (lidocaine base) | 4 |
| Anesthetic agent salt (prilocaine HCl) | 2 |

Preparation is similar to Example 25 with water and Carbopol 934P being used instead of propylene glycol and Klucel, respectively. A dispersion of 2 grams Carbopol 934 in 85 grams of water is prepared. A cream results form the above composition.

EXAMPLE 28

| Ingredient | % (w/w) |
|---|---|
| Binder (lecithin) | 7 |
| Solvent (propylene glycol) | 44 |
| Solvent (glycerin) | 7 |
| Thickener (Klucel, HF) | 2 |
| Anesthetic agent base (lidocaine base) | 27 |
| Anesthetic agent salt (dyclonine HCl) | 13 |

This ointment is prepared as in Example 25 with the appropriate substitution of ingredients to prepare this formulation.

EXAMPLE 29

Potassium Nitrate

| Ingredient | Formulation % (w/w) | | | |
|---|---|---|---|---|
|  | 1 | 2 | 3 | 4 |
| Tooth Sensitivity Treatment Agent (potassium nitrate) | 5 | 10 | 5 | 5 |
| Solvent (glycerin) | 42 | 37 | 38 | 40 |
| Solvent (dipropylene glycol) | 11 | 11 | 15 | 15 |
| Bioadhesive (karaya gum) | 42 | 42 | 42 | 40 |

EXAMPLE 30

Hydrocortisone

| Ingredient | Formulation % (w/w) | | | | |
|---|---|---|---|---|---|
|  | 1 | 2 | 3 | 4 | 5 |
| Corticosteroid (hydrocortisone) | 1 | 1 | 0.5 | 0.5 | 2.0 |
| Solvent (dipropylene glycol) | 15 | 15 | 15.5 | 11.5 | 15 |
| Solvent (glycerin) | 42 | 42 | 42 | 40 | 34 |
| Bioadhesive (karaya gum) | 42 | 26 | 26 | 48 | 34 |
| Bioadhesive (xantham gum) | — | 16 | 16 | — | — |
| Binder (lecithin) | — | — | — | — | 10 |
| Solvent (propylene glycol) | — | — | — | — | 5 |

EXAMPLE 31

| Ingredient | Formulation % w/w | | | |
|---|---|---|---|---|
|  | 1 | 2 | 3 | 4 |
| Coricosteroid (fluocinonide) | 0.05 | 0.05 | 0.05 | 0.1 |
| Solvent (propylene glycol) | 33.28 | 18.28 | 20.00 | 32.3 |
| Solvent (dipropylene glycol) | 0.0 | 15.00 | 13.28 | 0.0 |
| Solvent (glycerin) | 33.33 | 33.33 | 33.33 | 33.3 |
| Bioadhesive (karaya gum) | 33.34 | 33.34 | 28.34 | 33.4 |
| Bioadhesive (guar gum) | 0.0 | 0.0 | 5.00 | 0.0 |

EXAMPLE 32

|  | % (w/w) |
|---|---|
| Adrenocorticosteroid (betamethasone dipropionate) | 0.05 |
| Solvent (propylene glycol) | 33.28 |
| Solvent (glycerin) | 33.33 |
| Bioadhesive (karaya gum) | 33.34 |

EXAMPLE 33

|  | % (w/w) | | | |
|---|---|---|---|---|
|  | 1 | 2 | 3 | 4 |
| Antifungal (clotrimazole) | 1.0 | 1.0 | 2.0 | 1.0 |
| Adrenocorticosteroid (betamethasone dipropionate) | 0.05 | 0.05 | 0.05 | 0.05 |
| Solvent (dipropylene glycol) | 15.00 | 15.00 | 15.00 | 10.00 |
| Solvent (propylene glycol) | 15.00 | 15.00 | 15.00 | 15.00 |
| Solvent (glycerin) | 30.95 | 30.95 | 30.95 | 38.00 |
| Bioadhesive (karaya gum) | 38.0 | 0.0 | 0.0 | 35.95 |
| Bioadhesive (xantham gum) | 0.0 | 35.00 | 32.00 | 0.0 |
| Bioadhesive (pectin) | 0.0 | 3.00 | 6.00 | 0.0 |

EXAMPLE 34

|  | % (w/w) |
|---|---|
| Corticosteroid (mometasone furoate) | 0.1 |
| Solvent (propylene glycol) | 33.3 |
| Solvent (glycerin) | 33.3 |
| Bioadhesive | 33.3 |

EXAMPLE 35

|  | % (w/w) | | |
|---|---|---|---|
|  | 1 | 2 | 3 |
| Keratolytic Agent (salicylic acid) | 15 | 20 | 30 |

-continued

|  | % (w/w) | | |
| --- | --- | --- | --- |
|  | 1 | 2 | 3 |
| Solvent (glycerin) | 20 | 20 | 15 |
| Solvent (propylene glycol) | 15 | 15 | 15 |
| Solvent (dipropylene glycol) | 10 | 15 | 15 |
| Bioadhesive (karaya gum) | 40 | 30 | 25 |

EXAMPLE 36

|  | % (w/w) | | | | |
| --- | --- | --- | --- | --- | --- |
|  | 1 | 2 | 3 | 4 | 5 |
| Antineoplastic Agent (5-Aminolevulinic Acid) | 2 | 5 | 10 | 15 | 20 |
| Solvent (dipropylene glycol) | 10 | 10 | 15 | 15 | 15 |
| Solvent (oceic acid) | 10 | 10 | 10 | 10 | 10 |
| Solvent (glycerin) | 30 | 30 | 20 | 20 | 30 |
| Solvent (isocetyl alcohol) | — | — | 10 | 10 | — |
| Bioadhesive (karaya gum) | 30 | 30 | 20 | 20 | 30 |
| Bioadhesive (xantham gum) | — | — | 10 | 10 | — |
| Binder (lecithin) | 18 | 15 | 10 | 10 | — |

The foregoing examples are illustrative embodiments of the invention and are merely exemplary. A person skilled in the art may make variations and modification without departing from the spirit and scope of the invention. All such modifications and variations are intended to be included within the scope of the invention as described in this specification and the appended claims.

Indeed, the present invention is intended to encompass and be suitable for use by substituting any of the following drugs for the anesthetic agent as the pharmacologically active agent in the composition and methods for use of the same:

α-ADRENERGIC AGONIST such as Adrafinil, Adrenolone, Amidephrine, Apraclonidine, Budralazine, Clonidine, Cyclopentamine, Detomidine, Dimetofrine, Dipivefrin, Ephedrine, Epinephrine, Fenoxazoline, Guanabenz, Guanfacine, Hydroxyamphetamine, Ibopamine, Indanazoline, Isometheptene, Mephentermine, Metaraminol, Methoxamine, Methylhexaneamine, Metizolene, Midodrine, Naphazoline, Norepinephrine, Norfenefrine, Octodrine, Octopamine, Oxymetazoline, Phenylephrine, Phenylpropanolamine, Phenylpropylmethylamine, Pholedrine, Propylhexedrine, Pseudoephedrine, Rilmenidine, Synephrine, Tetrahydrozoline, Tiamenidine, Tramazoline, Tuaminoheptane, Tymazoline, Tyramine, Xylometazoline β-ADRENERGIC AGONIST such as Formoterol, Methoxyphenamine, Ritodrine, Terbuterol α-ADRENERGIC BLOCKER such as Dapiprazole, Doxazosin, Ergoloid Mesylates, Fenspiride, Prazosin, Terazosin, Tolazoline, Trimazosin, Yohimbine β-ADRENERGIC BLOCKER such as Acebutolol, Amosulalol, Arotinolol, Atenolol, Befunolol, Betaxolol, Bevantolol, Bisoprolol, Bopindolol, Bucumolol, Bufetolol, Bufuralol, Bunitrolol, Bupranolol, Butofilolol, Carazolol, Carteolol, Carvedilol, Celiprolol, Cetamolol, Cloranolol, Dilevalol, Epanolol, Esmolol, Indenolol, Labetalol, Levobunolol, Mepindolol, Metipranolol, Metoprolol, Moprolol, Nadolol, Nadoxolol, Nifenalol, Nipradilol, Oxprenolol, penbutolol, Pindolol, Practolol, Propranolol, Sotalol, Sulfinalol, Talinolol, Tertatolol, Timolol, Toliprolol, Xibenolol ALCOHOL DETERRENT such as Calcium Cyanamide Citrated, Disulfiram, Nitrefazole ALDOSE REDUCTASE INHIBITOR such as Epalrestat, Ponalrestat, Sorbinil, Tolrestat ANABOLIC such as Androisoxazole, Androstenediol, Bolandiol, Bolasterone, Clostebol, Ethylestrenol, Formyldienolone, 4-Hydroxy-19-nortestosterone, Methandriol, Methenolone, Methyltrienolone, Nandrolone, Nandrolone Decanoate, Nandrolone p-Hexyloxyphenyl-propionate, Nandrolone Phenpropionate, Norbolethone, Oxymesterone, Quinbolone, Stenbolone, Trenbolone ANALGESIC (DENTAL) such as Chlorobutanol, Clove, Eugenol, Potassium Nitrate, Potassium Oxalate ANALGESIC (NARCOTIC) such as Alfentanil, Allylprodine, Alphaprodine, Anileridine, Benzylmorphine, Bezitramide, Buprenorphine, Butorphanol, Clonitazene, Codeines, Desomorphine, Dextromoramide, Dezocine, Diampromide, Dihydrocodeine, Dihydrocodeinone Enol Acetate, Dihydromorphine, Dimenoxadol, Dimepheptanol, Dimethylthiambutene, Dioxaphetyl Butyrate, Dipipanone, Eptazocine, Ethoheptazine, Ethylmethlythiambutene, Ethylmorphine, Etonitazene, Fentanyl, Hydrocodone, Hydromorphone, Hydroxypethidine, Isomethadone, Ketobemidone, Levorphanol, Lofentanil, Meperidine, Meptazinol, Metazocine, Methadone, Metopon, Morphine, Morphine Derivatives, Myrophine, Nalbuphine, Narceine, Nicomorphine, Norlevorphanol, Normethadone, Normorphine, Norpipanone, Opium, Oxycodone, Oxymorphone, Papaveretum, Pentazocine, Phenadoxone, Phenazocine, Pheoperidine, Piminodine, Piritramide, Proheptazine, Promedol, Properidine, Propiram, Propoxyphene, Sufentanil, Tilidine ANALGESIC (NON-NARCOTIC) such as Acetaminophen, Acetaminosalol, Acetanilide, Acetylsalicylates, Acetylsalicylsalicylic Acid, Alclofenac, Alminoprofen, Aloxiprin, Aluminum Bis(acetylsalicylate),Aminochlorthenoxazin, 2-Amino-4-picoline, Aminopropylon, Aminopyrine, Antipyrine, Antipyrine Salicylate, Antrafenine, Apazone, Aspirin, Benorylate, Benoxaprofen, Benzpiperylon, Benzydamine, p-Bromoacetanilide, 5-Bromosalicylic Acid Acetate, Bufexamac, Bucetin, Bumadizon, Butacetin, Carbamazepine, Carbetidine, Carbiphene, Carsalam, Chloralantipyrine, Chlorthenoxazin (e), Choline Salicylate, Cinchophen, Ciramadol, Clometacin, Cropropamide, Crotethamide, Dexoxadrol, Difenamizole, Diflunisal, Dipyrocetyl, Dipyrone, Emorfazone, Enfenamic Acid, Epirizole, Etersalate, Ethenzamide, Ethoxazene, Etodolac, Felbinac, Fenoprofen, Floctafenine, Flufenamic Acid, Fluoresone, Flupirtine, Fluproquazone, Flurbiprofen, Fosfosal, Gentisic Acid, Glafenine, Ibufenac, Imidazole Salicylate, Indomethacin, Indoprofen, Isofezolac, Isoladol, Isonixin, Ketoprofen, Ketorolac, p-Lactophenetide, Lefetamine, Loxoprofen, Lysine Acetylsalicylate, Methotrimepraz ine, Metofoline, Miroprofen, Morazone, Morpholine Salicylate, Naproxen, Nefopam, Nifenazone, 5' Nitro-2' propoxyacetanilide, Parsalmide, Perisoxal, Phenacetin, Phenazopyridine, Phenocoll, Phenopyrazone, Phenyl Acetylsalicylate, Phenyl Salicylate, Phenyramidol, Pipebuzone, Piperylone, Prodilidine, Propacetamol, Propyphenazone, Proxazole, Quinine Salicylate, Ramifenazone, Rimazolium Metilsulfate, Salacetamide, Salicin, Salicylamide, Salicylamide
O-Acetic Acid, Salicylic Acid, Salicylates and Derivatives, Salicylsulfuric Acid, Salsalte, Salverine, Simetride, Sulfamipyrine, Suprofen, Talniflumate, Tenoxicam, Terofenamate, Tetradrine, Tinoridine, Tolfenamic Acid, Tolpronine, Tramadol, Viminol, Xenbucin, Zomepirac ANDROGEN such as Boldenone, Fluoxymesterone, Mestanolone, Mesterolone, Methandrostenolone, 17-Methyltestosterone, 17α-Methyl-testosterone 3-Cyclopentyl Enol Ether, Norethandrolone, Normethandrone, Oxandrolone, Oxymetholone, Prasterone, Stanlolone, Stanozolol, Testosterone, Testosterone 17-Chloral Hemiacetal, Testosterone 17β-Cypionate, Testosterone Enanthate, Testosterone Nicotinate, Testosterone Pheynylacetate, Testosterone Propionate, Tiomesterone ANESTHETIC such as Acetamidoeugenol, Alfadolone Acetate, Alfaxalone, Amucaine, Amolanone, Amylocaine, Benoxinate, Betoxycaine, Biphenamine, Bupivacaine, Burethamine, Butacaine, Butaben, Butanilicaine, Buthalital, Butoxycaine, Carticaine, 2-Chloroprocaine, Cocaethylene, Cocaine, Cyclomethycaine, Dibucaine, Dimethisoquin, Dimethocaine, Diperadon, Dyclonine, Ecgonidine, Ecgonine, Ethyl Aminobenzoate, Ethyl Chloride, Etidocaine, Etoxadrol, β-Eucaine, Euprocin, Fenalcomine, Fomocaine, Hexobarbital, Hexylcaine, Hydroxydione, Hydroxyprocaine, Hydroxytetracaine, Isobutyl p-Aminobenzoate, Kentamine, Leucinocaine Mesylate, Levoxadrol, Lidocaine, Mepivacaine, Meprylcaine, Metabutoxycaine, Methohexital, Methyl Chloride, Midazolam, Myrtecaine, Naepaine, Octacaine, Orthocaine, Oxethazaine, Parethoxycaine, Phenacaine, Phencyclidine, Phenol, Piperocaine, Piridocaine, Polidocanol, Pramoxine, Prilocaine, Procaine, Propanidid, Propanocaine, Proparacaine, Propipocaine, Propofol, Propoxycaine, Pseudococaine, Pyrrocaine, Risocaine, Salicyl Alcohol, Tetracaine, Thialbarbital, Thimylal, Thiobutabarbital, Thiopental, Tolycaine, Trimecaine, Zolamine ANOREXIC such as Aminorex, Amphecloral, Benzaphetamine, Chlorphentermine, Clobenzorex, Cloforex, Cyclexedrine, Diphemethoxidine, Fenbutrazate, Fenfluramine, Fenproporex, Furfurylmethylamphetamine, Levophacetoperate, Mefenorex, Metamfeproamone, Norpseudoephedrine, Phenpentermine, Picilorex ANTHELMINTIC (CESTODES) such as Arecoline, Aspidin, Aspidinol, Dichlorophen(e), Embelin, Kosin, Napthalene, Niclosamide, Pellertierine, Pellertierine Tannate, Quinacrine ANTHELMINTIC (NEMATODES) such as Alantolactone, Amoscanate, Ascaridole, Bephenium, Bitoscanate, Carbon Tetrachloride, Carvacrol, Cyclobendazole, Diethylcarbamazine, Diphenane, Dithiazanine Iodide, Dymanthine, Gentian Violet, 4-Hexylresorcinol, Kainic Acid, Mebendazole, 2-Napthol, Oxantel, Piperazines, Pyrantel, Pyrvinium Pamoate, α-Santonin, Stilbazium Iodide, Tetrachloroethylene, Thiabendazole, Thymol, Thymyl N-soamylcarbamate, Triclofenol Piperazine, Urea Stibamine ANTHELMINTIC (ONCHOCERCA) such as Ivermectin ANTHELMINTIC (SCHISTOSOMA) such as Amphotalide, Antimony(s) and Derivatives, Becanthone, Hycanthone, Lucanthone, Niridazole, Oxamniquine, Praziquantel, Stibocaptate, Stibophen ANTHELMINTIC (TREMATODES) such as Anthiolimine ANTIACNE such as Algestone Acetophenide, Azelaic Acid, Benzoyl Peroxide, Dichloroacetic Acid, Motretinide, Retinoic Acid, Tetroquinone ANTIALLERGIC such as Amlexanox, Astemizole, Azelastine, Cromolyn, Fenpiprane, Histamines, Ketotifen, Nedocromil, Oxatomide, Pentigetide, Poison Ivy Extract, Poison Oak Extract, Poison Sumac Extract, Repirinast, Tiaramide, Tranilast, Traxanox, Urushiol ANTIAMEBIC such as Arsthinol, Bialamicol, Carbarsone, Cephaeline, Chlorbetamide, Chlorphenoxamide, Dehydroemetine, Dibromopropamidine, Diloxanide, Dephetarsone, Emetine, Fumagillin, Glaucarubin, Glycobiarsol, 8-Hydroxy-7-iodo-5-quinolinesulfonic Acid, Iodochlorhydroxyquin, Iodoquinol, Paromomycin, Phanquinone, Phearsone Sulfoxylate, Polybenzarsol, Propamidine, Quinfamide, Secnidazole, Sulfarside, Teclozan, Thiocarbamizine, Thiocarbarsone, Tinidazole ANTIANDROGEN such as Bifluranol, Cyoctol, Cyproterone, Oxendolone ANTIANGINAL such as Amlodipine, Amyl Nitrite, Cinepazet Maleate, Imolamine, Isosorbide Dinitrate, Limaprost, Molsidomine, Nitroxyalklamide Derivatives ANTIARRHYTHMIC such as Acecaine, Adenosine, Ajmaline, Alprenolol, s-Aminoalkyl-s-Arylsulfoximines, Amoproxan, Aprindine, Bretylium Tosylate, Bubumolol, Bunaftine, Butidrine, Butobendine, Capobenic Acid, Cifenline, Disopyramide, Encainide, Flecainide, Hydroquinidine, Indecainide, Ipratropium, Lorajmine, Lorcainide, Meobentine, Mexiletine, Moricizine, Pirmenol, Prajmaline, Procainamide, Pronethalol, Propafenone, Pyrinoline, Quinidine, Quinidine Sulfate, Quinidine, Tocainide, Viquidil ANTIARTERIOSCLEROTIC such as Pyridinol Carbamate ANTIARTHRITIC/ANTIRHEUMATIC such as Allocupreide Sodium, Auranofin, Aurothioglucose, Aurothioglycanide, Azathioprine, Di-tert-Butylphenols, Calcium3-Aurothio-2-propanol-1-sulfonate, Clobuzarit, Cuproxoline, Diacerein, Glucosamine, Gold Sodium Thiomalate, Gold Sodium Thiosulfate, Hydroxychloroquine, Kebuzone, Lobenzarit, Melittin, Myoral, Penicillamine

ANTIBACTERIAL (ANTIBIOTIC)

Aminoglycosides such as Amikacin, Apramycin, Arbekacin, Bambermycins, Butirosin, Dibekacin, Dihdrostreptomycin, Fortimicin(s), Fradiomycin, Gentamicin, Ispamicin, Kanamycin, Micronomicin, Neomycin, Neomycin Undecylenate, Netilmicin, Paromomycin, Ribostamycin, Sisomicin, Spectinomycin, Streptomycin, Streptonicozid, Tobramycin Amphenicols such as Azidamfenicol, Chloramphenicol, Chloramphenicol Palmirate, Chloramphenicol Pantothenate, Florfenicol, Thiamphenicol Ansamycins such as Rifamide, Rifampin, Rifamycin, Rifaximin β-Lactams Carbapenems such as Imipenem Cephalosporins such as 1-Carba (dethia) Cephalosporin, Cefactor, Cefadroxil, Cefamandole, Cefatrizine, Cefazedone, Cefazolin, Cefixime, Cefmenoxime, Cefodizime, Cefonicid, Cefoperazone, Ceforanide, Cefotaxime, Cefotiam, Cefpimizole, Cefpiramide, Cefpodoxime Proxetil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine, Pivcefalexin Cephamycins such as Cefbuperazone, Cefmetazole, Cefminox, Cefetan, Cefoxitin Monobactams such as Aztreonam, Carumonam, Tigemonam Oxacephems such as Flomoxef, Moxolactam Penicillins such as Amidinocillin, Amdinocillin Pivoxil, Amoxicillin, Ampicillan, Apalcillin, Aspoxicillin, Azidocillan, Azlocillan, Bacampicillin, Benzylpenicillinic Acid, Benzylpenicillin, Carbenicillin, Carfecillin, Carindacillin, Clometocillin, Cloxacillin, Cyclacillin, Dicloxacillin, Diphenicillin, Epicillin, Fenbenicillin, Floxicillin, Hetacillin, Lenampicillin, Metampicillin, Methicillin, Mezlocillin, Nafcillin, Oxacillin, Penamecillin, Penethamate Hydriodide, Penicillin G Benethamine, Penicillin G Benzathine, Penicillin G Benzhydrylamine, Penicillin G Calcium, Penicillin G Hydrabamine, Penicillin G Potassium, Penicillin G Procaine, Penicillin N, Penicillin O, Penicillin V, Penicillin V Benzathine, Penicillin V Hydrabamine, Penimepicycline, Phenethicillin, Piperacillin, Pivapicillin, Propicillin, Quinacillin, Sulbenicillin, Talampicillin, Temocillin, Ticarcillin Lincosamides such as Clindamycin, Lincomycin Macrolides such as Azithromycin, Carbomycin, Clarithromycin, Erythromycin(s) and Derivatives, Josamycin, Leucomycins, Midecamycins, Miokamycin, Oleandomycin, Primycin, Rokitamycin, Rosaramicin, Roxithromycin, Spiramycin, Troleandomycin Polypeptides such as Amphomycin, Bacitracin, Capreomycin, Colistin, Enduracidin, Enviomycin, Fusafungine, Gramicidin(s), Gramicidin S, Mikamycin, Polymyxin, Polymyxin B-Methanesulfonic Acid, Pristinamycin, Ristocetin, Teicoplanin, Thiostrepton, Tuberactinomycin, Tyrocidine, Tyrothricin, Vancomycin, Viomycin(s), Virginiamycin, Zinc Bacitracin Tetracyclines such as Apicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Senociclin, Tetracycline Others such as Cycloserine, Mupirocin, Tuberin,

ANTIBACTERIAL (SYNTHETIC)

2,4-Diaminopyrimidines such as Brodimoprim, Tetroxoprim, Trimethoprim

Nitrofurans such as Furaltadone, Furazolium, Nifuradene, Nifuratel, Nifurfoline, Nifurpirinol, Nifurprazine, Nifurtoinol, Nitrofurantoin Quinolones and Analogs such as Amifloxacin, Cinoxacin, Ciprofloxacin, Difloxacin, Enoxacin, Fleroxacin, Flumequine, Lomefloxacin, Miloxacin, Nalidixic Acid, Norfloxacin, Ofloxacin, Oxolinic Acid, Pefloxacin, Pipemidic Acid, Piromidic Acid, Rosoxacin, Temafloxacin, Tosufloxacin Sulfonamides such as Acetyl Sulfamethoxypyrazine, Acetyl Sulfisoxazole, Azosulfamide, Benzylsulfamide, Chloramine-B, Chloramine-T, Dichloramine T, Formosulfathiazole, $N^2$-Formyl-sulfisomidine, $N^4$-$\beta$-D-Glucosylsulfanilamide, Mafenide, 4'-(Methyl-sulfamoyl)sulfanilanilide, p-Nitrosulfathiazole, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfametrole, Sulfamidochrysoidine, Sulfamoxole, Sulfanilamide, Sulfanilamidomethanesulfonic Acid Triethanolamine Salt, 4-Sulfanilamidosalicylic Acid, $N^4$-Sulfanilylsulfanilamide, Sulfanilylurea, N-Sulfanilyl-3,4-xylamide, Sulfanitran, Sulfaperine, Sulfaphenazole, Sulfaproxyline, Sulfapyrazine, Sulfapyridine, Sulfasomizole, Sulfasymazine, Sulfathiazole, Sulfathiourea, Sulfatolamide, Sulfisomidine, Sulfisoxazole Sulfones such as Acedapsone, Acediasulfone, Acetosulfone, Dapsone, Diathymosulfone, Glucosulfone, Solasulfone, Succisulfone, Sulfanilic Acid, p-Sulfanilylbenzylamine, p,p'-Sulfonyldianiline-N,N' digalactoside, Sulfoxone, Thiazolsulfone Others such as Clofoctol, Hexedine, Magainins, Methenamine, Methenamine Anhydromethylene-citrate, Methenamine Hippurate, Methenamine Mandelate, Methenamine Sulfosalicylate, Nitroxoline, Squalamine, Xibornol ANTICHOLINERGIC such as Adiphenine, Alverine, Ambutonomium, Aminopentamide, Amixetrine, Amprotropine Phosphate, Anisotropine Methylbromide, Apoatropine, Atropine, Atropine N-Oxide, Benactyzine, Benapryzine, Benzetimide, Benzilonium, Benztropine Mesylate, Bevonium Methyl Sulfate, Biperiden, Butropium, N-Butylscopolammonium Bromide, Buzepide, Camylofine, Caramiphen, Chlorbenzoxamine, Chlorphenoxamine, Cimetropium, Clidinium, Cyclodrine, Cyclonium, Cyclopentolate, Cycrimine, Deptropine, Dexetimide, Dibutoline Sulfate, Dicyclomine, Diethazine, Difemerine, Dihexyverine, Diphemanil Methylsulfate, N-(1,2-Diphenylethyl)nicotinamide, Dipiproverine, Diponium, Emepronium, Endobenzyline, Ethopropazine, Ethybenztropine, Ethylbenzhydramine, Etomidoline, Eucatropine, Fenpiverinium, Fentonium, Flutropium, Glycopyrrolate, Heteronium, Hexocyclium Methyl Sulfate, Homatropine, Homatropine Methyl Bromide, Hyoscyamine, Ipratropium, Isopropamide, Levomepate, Mecloxamine, Mepenzolate, Metcaraphen, Methantheline, Methixene, Methscopolamine, Octamylamine, Oxybutynin, Oxyphencyclimine, Oxyphenonium, Pentapiperide, Penthienate, Phencarbamide, Phenglutarimide, Pipenzolate, Piperidolate, Piperilate, Poldine Methysulfate, Pridinol, Prifinium, Procyclidine, Propantheline, Propenzolate, Propyromazine, Scopolamine N-Oxide, Stilonium, Stramonium, Sultroponium, Thihexinol, Thiphenamil, Tiemonium, Timepidium, Tiquizium, Tridihexethyl Iodide, Trihexyphenidyl Hydrochloride, Tropacine, Tropenzile, Tropicamide, Trospium, Valethamate, Xenytropium ANTICONVULSANT such as Acetylpheneturide, Albutoin, Aloxidone, Aminoglutethimide, 4-Amino-3-hydroxybutyric Acid, Atrolactamide, Beclamide, Buramate, Carbamazepine, Cinromide, Clonazepam, Decimemide, Diethadione, Dimethadione, Doxenitoin, Eterobarb, Ethadione, Ethosuximide, Ethotoin, Fluoresone, 5-Hydroxytryptophan, Lamotrigine, Magnesium Sulfate, Mephenytoin, Metharbital, Methetoin, Methsuximide, 5-Methyl-5-( 3-phenanthryl)-hydantoin, 3-Methyl-5-phenylhydantoin, Narcobarbital, Nimetazepam, Nitrazepam, Paramethadione, Phenacemide, Phenceturide, Phensuximide, Phenytoin, Phethenylate Sodium, Primidone, Progabide, Solanum, Strontium, Suclofenide, Sulthiame, Tetrantoin, Trimethadione, Valproic Acid, Valpromide, Vigabatrin, Zonisamide

ANTIDEPRESSANT

Bicyclics such as Binedaline, Caroxazone, Citalopram, Dimethazan, Indalpine, Fencamine, Indeloxazine, Nefopam, Nomifensine, Oxitriptan, Oxypertine, Paroxetine, Sertraline, Thiazesim, Trazodone, Zometapine Hydrazides/Hydrazines such as Benmoxine, Iproclozide, Iproniazid, Isocarboxazid, Nialamide, Octamoxin, Phenelzine Pyrrolidones such as Cotinine, Rolicyprine, Rolipram Tetracyclics such as Maprotiline, Metralindole, Mianserin, Oxaprotiline Tricyclics such as Adinazolam, Amitriptyline, Amitriptylinoxide, Amoxapine, Butriptyline, Clomipramine, Demexiptiline, Desipramine, Dibenzepin, Dimetacrine, Dothiepin, Doxepin, Fluacizine, Imipramine, Imipramine N-Oxide, Iprindole, Lofepramine, Melitracen, Metapramine, Nortriptyline, Noxiptilin, Opipramol, Propizepine, Protriptyline, Quinupramine, Tianeptine, Trimipramine Others such as Benactyzine, Bupropion, Butacetin, Deanol, Deanol Aceglumate, Deanol Acetamidobenzoate, Dioxadrol, Etoperidone, Febarbamate, Femoxetine, Fenpentadiol, Fluoxetine, Fluvoxamine, Hematoporphyrin, Hypercinin, Levophacetoperane, Lithium, Medifoxamine, Minaprine, Moclobemide, Oxaflozane, Piberaline, Polycyclic Imides, Prolintane, Pyrisuccideanol, Rubidium, Sulpiride, Sultopride, Teniloxazine, Thozalinone, Tofenacin, Toloxatone, Tranylcypromine, L-Tryptophan, Viloxazine, Zimeldine

ANTIDIABETIC

Biguanides such as Buformin, Metformin, Phenformin

Sulfonylurea Derivatives such as Acetohexamide, 1-Butyl-3-metanilylurea, Carbutamide, Chlorpropamide, Glibornuride, Gliclazide, Glimepiride, Glipizide, Gliquidone, Glisoxepid, Glyburide, Glybuthiazol(e), Glybuzole, Glyhexamide, Glymidine, Glypinamide, Phenbutamide, Tolazamide, Tolbutamide, Tolcyclamide Others such as Acarbose, Benzylthiazolidene-2,4-dione, Calcium Mesoxalate, Miglitol ANTIDIARRHEAL such as Acetyltannic Acid, Albumin Tannate, Alkofanone, Aluminum Salicylates, Catechin, Difenoxin, Diphenoxylate, Lidamidine, Loperamide, Mebiquine, Trillium, Uzarin ANTIDIURETIC such as Desmopressin, Felypressin, Lypressin, Ornipressin, Oxycinchophen, Terlipressin, Vasopressin ANTIESTROGEN such as Delmadinone Acetate, Ethamoxytriphetol, Tamoxifen, Toremifene

ANTIFUNGAL (ANTIBIOTICS)

Polyenes such as Amphotericin-B, Candicidin, Dermostatin, Filipin, Fungichromin, Hachimycin, Hamycin, Lucensomycin, Mepartricin, Natamycin, Nystatin, Pecilocin, Perimycin Others such as Azaserine, Griseofulvin, Oligomycins, Pyrrolnitrin, Siccanin, Tubercidin, Viridin

ANTIFUNGAL ( SYNTHETIC )

Allylamines such as Naftifine, Terbinafine

Imidazoles such as Bifonazole, Butoconazole, Chlordantoin, Chlormidazole, Cloconazole, Clotrimazole, Econazole, Enilconazole, Fenticonazole, Isoconazole, Ketoconazole, Miconazole, Omoconazole, Oxiconazole Nitrate, Sulconazole, Tioconazole Triazoles such as Fluconazole, Itraconazole, Terconazole Others such as Acrisorcin, Amorolfine, Biphenamine, Bromosalicylchloranilide, Buclosamide, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionates, Propionic Acid, Pyrithione, Salicylanilide, Sulbentine, Tenonitrozole, Tolciclate, Tolindate, Tolnaftate, Tricetin, Ujothion, Undecylenic Acid ANTIGLAUCOMA such as Dapiprazoke, Dichlorphenamide, Dipivefrin, Pilocarpine ANTIGONADOTROPIN such as Danazol, Gestrinone, Paroxypropione ANTIGOUT such as Colchicine, Probenecid, Sulfinpyrazone

ANTIHISTAMINIC

Alkylamine Derivatives such as Acrivastine, Bamipine, Brompheniramine, Chlorpheniramine, Dimethindene, Metron S, Pheniramine, Pyrrobutamine, Thenaldine, Tolpropamine, Triprolidine Aminoalkyl Ethers such as Bietanautine, Bromodiphenhydramine, Carbinoxamine, Clemastine, Diphenlypyraline, Doxylamine, Embrammine, Medrylamine, Mephenphydramine, p-Methyldiphenhydramine, Orphenadr ine, Phenyltoloxamine, Piprinhydrinate, Setasine Ethylenediamine Derivatives such as Alloclamide, p-Bromtripelennamine, Chloropyramine, Chlorothen, Histapyrrodine, Methafurylene, Methaphenilene, Methapyrilene, Phenbenzamine, Pyrilamine, Talastine, Thenyldiamine, Thonzylamine, Tripelennamine, Zolamine Piperazines such as Cetirizine, Chlorcyclizine, Clocinizine, Hydroxyzine Tricyclics Phenothiazines such as Ahistan, Etymemazine, Fenethazine, N-Hydroxyethylpromethazine, Isopromethazine, Mequitaz inc, Promethazine, Pyrathiazine, Thiazinamium Methyl Sulfate Others such as Azatadine, Clobenzepam, Cyproheptadine, Deptropine, Isothipendyl, Loratadine, Prothipendyl Others such as Antazoline, Cetoxime, Clemizole, Clobenztropine, Diphenazoline, Diphenhydramine, Mebhydroline, Phenindamine, Terfenadine, Tritoqualine

ANTIHYPERLIPOPROTEINEMIC

Aryloxyalkanoic Acid Derivatives such as Beclorbrate, Bazafibrate, Binifibrate, Ciprofibrate, Clinofibrate, Clofibrate, Clofibric Acid, Etonfibrate, Fenofibrate, Gemfibrozil, Nicofibrate, Pirifibrate, Ronifibrate, Simfibrate, Theofibrate Bile Acid Sequesterants such as Cholestyramine Resin, Colestipol, Polidexide HMG CoA Reductase Inhibitors such as Lovastatin, Pravastatin, Simvastatin Nicotinic Acid Derivatives Aluminum Nicotinate, Acipimox, Niceritrol, Nicoclonate, Nicomol, Oxiniacic Acid Thyroid Hormones/Analogs such as Etiroxate, Thyropropic Acid Others such as Acifran, Azacosterol, Benfluorex, β-Benzalbutyramide, Benzodioxole, Carnitine, Chondroitin Sulfate, Clomestone, Detaxtran, Dextran Sulfate Sodium, 5,8,11,14,17-Eicosapentaenoic Acid, Eritadenine, Farnesylated tetrahydro-naphthalenols, Furazbol, Meglutol, Melinamide, Mytatrienediol, Naphtyl-tetrahydronaphtyl-diphosPhonates, Ornithine, γ-Oryzanol, Pantethine, Penataerythritol Tetraacetate, α-Phenylbutyramide, Phylate Acids and Salts, Pirozadil, Probucol, α-Sitosterol, Sultosilic Acid, Tiadenol, Triparanol

ANTIHYPERTENSIVE

Benzothiadiazine Derivatives such as Althiazide, Bendroflumethiazide, Benzthiazide, Benzylhydrochlorothiazide, Buthiazide, Chlorothiazide, Chlorthalidone, Cyclopenthiazide, Cyclothiazide, Diazoxide, Epithiazide, Ethiazide, Fenquizone, Hydrochlorothiazide, Hydroflumethiazide, Methyclothiazide, Meticrane, Metolazone, paraflutizide, polythiazide, Tetrachlormethiazide, Trichlormethiazide N-Carboxyalkyl (peptide/lactam) Derivatives such as Alacepril, Captopril, Cilazapril, Delapril, Enalapril, Enalaprilat, Fosinopril, Lisinopril, Moveltipril, perindopril, Quinapril, Ramipril Guanidine Derivatives Bethanidine, Debrisoquin, Guanacline, Guanadrel, Guanazodine, Guanethidine, Guanochlor, Guanoxabenz, Guanoxan Hydrazines/Phthalazines such as Cadralazine, Dihydralazine, Endralazine, Hydracarbazine, Hydralazine, Pheniprazine, Pildralazine, Todralazine Imidazole Derivatives such as Lofexidine, Phentolamine, Tolonidine Quaternary Ammonium Compounds Azamethonium, Chlorisondamine, Hexamethonium, Pentacynium Bis(methyl sulfate), Pentamethonium, Pentolinium Tartate, Phenactopinium, Trimethidiunum Methosulfate Quinazoline Derivatives such as Alfuzosin, Bunazosin Reserpine Derivatives such as Bietaserpine, Deserpidine, Rescinnamine, Reserpine, Syrosingopine Sulfonamide Derivatives such as Ambuside, Clopamide, Furosemide, Indapamide, Quinethazone, Tripamide, Xipamide Others such as Aimaline, γ-Aminobutyric Acid, Bufeniode, Chlorthalidone, Cicletaine, Ciclosidomine, Cryptenamine Tannates, Flosequinan, Indoramin, Ketanserin, Metbutamate, Mecamylamine, Methyldopa, Methyl 4-Pyridyl Ketone Thiosemicarbarzone, Metolazone, Minoxidil, Muzolimine, Pargyline, Pempidine, Pinacidil, Piperoxan, Primaperone, Propargyl Glycine Aminopropargyl Diols, Protoveratrines, Raubasine, Rescimetol, Saralasin, Sodium Nitroprusside, Ticrynafen, Trimethaphan Camsylate, Tyrosinase, Urapidil ANTIHYPERTHYROID such as 2-Amino-4-methylthiazole, 2-Aminothiazole, Carbimazole, 3,5-Dibromo-L-tyrosine, 3,5-Diiodotyrosine, Hinderin, Iodine, Iothiouracil, Methimazole, Methylthiouracil, Propylthiouracil, Sodium Perchlorate, Thibenzazoline, Thiobarbital, 2-Thiouracil ANTIHYPOTENSIVE such as Amezinium Methyl Sulfate, Angiotensin Amide, Etifelmin, Etilefrin, Gepefrine ANTIHYPOTHYROID such as Levothyroxine, Liothyronine, Thyroid, Thyroidin, Thyroxine, Tiratricol

ANTI-INFLAMMATORY (NONSTEROIDAL)

Aminoarylcarboxylic Acid Derivatives such as Etofenamate, Meclofenamic Acid, Mefanamic Acid, Niflumic Acid Arylacetic Acid Derivatives such as Acemetacin, Amfenac, Cinmetacin, Clopirac, Diclofenac, Fenclofenac, Fenclorac, Fenclozic Acid, Fentiazac, Glucametacin, Isoxepac, Lonazolac, Metiazinic Acid, Oxametacine, Proglumetacin, Sulindac, Tiaramide, Tolmetin Arylbutyric Acid Derivatives such as Butibufen, Fenbufen Arylcarboxylic Acids such as Clidanac, Ketorolac, Tinoridine Arylpropionic Acid Derivatives such as Bucloxic Acid, Carprofen, Fenoprofen, Flunoxaprofen, Ibuprofen, Ibuproxam, Oxaprozin, Piketoprofen, Pirprofen, Pranoprofen, Protizinic Acid, Tiaprofenic Acid Pyrazoles such as Mepirizole Pyrazolones such as Clofezone, Feprazone, Mofebutazone, Oxyphenbutazone, Phenylbutazone, Phenyl Pyrazolidininones, Suxibuzone, Thiazolinobutazone Salicylic Acid Derivatives such as Bromosaligenin, Fendosal, Glycol Salicylate, Mesalamine, 1-Naphthyl Salicylate, Olsalazine, Sulfasalazine Thiazinecarboxamides such as Droxicam, Isoxicam, Piroxicam Others such as ε-Acetamidocaproic Acid, S-Adenosylmethionine, 3-Amino-4-hydroxybutyric Acid, Amixetrine, Bendazac, Bucolome, Carbazones, Difenpiramide, Ditazol, Guaiazulene, Heterocylic Aminoalkyl Esters of Mycophenolic Acid and Derivatives, Nabumetone, Nimesulide, Orgotein, Oxaceprol, Oxazole Derivatives, Paranyline, Pifoxime, 2-substituted-4, 6-di-tertiary-butyl-s-hydroxy-1,3-pyrimidines, Proquazone, Sialyl Lewis$^x$ Dimers, Tenidap ANTIMALARIAL such as Acedapsone, Alphaaminoquinolines, 4-Aminoquinolines, Amodiaquin, Arteether, Artemether, Artemisinin, Artesunate, Bebeerine, Berberine, Chirata, Chlorguanide, Chloroquine, Chlorproguanil, Cinchona, Cinchonidine, Cinchonine, Cycloguanil, Euquinine, Gentiopicrin, Halofantrine, Mefloquine Hydrochloride, 3-Methylarsacetin, Pamaquine, Plasmocid, Primaquine, Pyrimethamine, Quinacrine, Quinine (Acids, Salts and Derivatives), Quinine Formate, Quinine Gluconate, Quinine Tannate, Quinine Urea Hydrochloride, Quinocide, Quinoform, Quinoline, Sodium Arsenate, Diabasic ANTIMIGRAINE such as Alpiropride, Dihydroergotamine, Ergocornine, Ergocorninine, Ergocryptine, Ergot, Ergotamine, Flumedroxone Acetate, Fonazine, Methysergid(e), Oxetorone, Pizotyline, Sumatriptan ANTINAUSEANT such as Acetylleucine Monoethanolamine, Bietanautine, Bromopride, Buclizine, Clebopride, Cyclizine, Dimenhydrinate, Diphenidodol, Domperidone, Granisetron, Meclizine, Methalltal, Metoclopramide, Metopimazine, Nabilone, Ondansteron, Oxypendyl, Pipamazine, Piprinhydrinate, Scopolamine, Tetrahydrocannabinols, Thiethylperazine, Trimethobenzamide

ANTINEOPLASTIC

Alkylating agents

Alkyl Sulfonates such as Busulfan, Improsulfan, Piposulfan

Aziridines such as Benzodepa, Carboquone, Meturedepa, Uredepa

Ethylenimines and Methylmelamines such as Altretamine, Triethylenemelamine, Triethylenephosphoramide, Triethylenethiophosphoramide, Trimethylolomelamine Nitrogen Mustards such as Chlorambucil, Chlornaphazine, Chclophosphamide, Estramustine, Ifosfamide, Mechlorethamine, Mechlorethamine Oxide Hydrochloride, Melphalan, Novembichin, Phenesterine, prednimustine, Trofosfamide, Uracil Mustard Nitrosoureas Carmustine, Chlorozotocin, Fotemustine, Lomustine, Nimustine, Ranimustine Others such as Dacarbazine, Mannomustine, Mitobronitol, Mitolactol, Pipobroman Antibiotics such as Aclacinomycins, Actinomycin $F_1$, Anthramycin, Azaserine, Bleomycins, Cactinomycin, Carubicin, Carzinophilin, Chromomycins, Dactinomycin, Daunorubicin, 6-Diazo-5-oxo-L-norleucine, Doxorubicin, Epirubicin, Mitomycins, Mycophenolic Acid, Nogalamycin, Olivomycins, Peplomycin, Plicamycin, porfiromycin, Puromycin, Streptonigrin, Streptozocin, Tubercidin, Ubenimex, Zinostatin, Zorubicin Antimetabolites Folic Acid Analogs such as Denopterin, Methotrexate, Pteropterin, Trimetrexate Purine Analogs such as Fludarabine, 6-Mercaptopurine, Thiamiprine, Thioguanaine Pyrimidine Analogs such as Ancitabine, Azacitidine, 6-Azauridine, Carmofur, Cytarabine, Dideoxyuridines, Doxifluridine, Enocitabine, Floxuridine, Fluororacil, Tegafur Enzymes such as L-Asparaginase, Pulmozyme Others such as Aceglatone, Aldophophamide Glycoside, Aminolevulinic Acid, Amsacrine, Bestrabucil, Bisantrene, Carboplatin, Cisplatin, Defofamide, Demecolcine, Diaziquone, Elfornithine, Elliptinium Acetate, Etoglucid, Etoposide, Gallium Nitrate, Hydroxyurea, Interferon-$\alpha$, Interferon-$\beta$, Interferon-$\gamma$, Interleukine-2, Lentinan, Lonidamine, Mitoguazone, Mitoxantrone, Mopidamol, Nitracrine, Pentostatin, Phenamet, Pirarubicin, podophyllinicc Acid, 2-Ethythydrazide, Procarbazine, PSK®, Razoxane, Sizofiran, Spirogermanium, Taxol, Teniposide, Tenuazonic Acid, Triaziquone, 2,2',2''-Trichlorotriethylamine, Urethan, Vinblastine, Vincristine, Vindesine

ANTINEOPLASTIC (HORMONAL)

Androgens such as Calusterone, Dromostanolone Propionate, Epitiostanol, Mepitiostane, Testolactone Antiadrenals such as Aminoglutethimide, Mitotane, Trilostane Antiandrogens such as Flutamide, Nilutamide Antiestrogens such as Aromatase Inhibiting 4(5)-Imidazoles

ANTINEOPLASTIC ADJUNCT

Folic Acid Replenisher such as Frolinic Acid

ANTIPARKINSONIAN such as Amantadine, Benserazide, Bietanautine, Biperiden, Budipine, Carbidopa, Deprenyl, Dexetimide, Diethazine, Droxidopa, Ethopropazine, Ethylbenzhydramine, Levodopa, Piroheptine, Pridinol, Prodipine, Terguride, Tiapride, Tigloidine ANTIPHEOCHROMOCYTOMA such as Metyrosine, Phenoxybenzamine ANTIPNEUMOCYSTIS such as Effornithine ANTIPROSTATIC HYPERTROPHY such as Proscar®

ANTIPROTOZOAL (LEISHMANIA) such as Ethylstibamine, Hydroxystilbamidine, N-Methylglucamine, Pentamidine, Stilbamidine ANTIPROTOZOAL (TRICHOMONAS) such as Acetarsone, Aminitrozole, Anisomycin, Azanidazole, Forminitrazole, Furazolidone, Hachimycin, Lauroguadine, Metronidazole, Nifuratel, Nimorazole, Silver Picrate, Tenonitrozole ANTIPROTOZOAL (TRYPANOSOMA) such as Benznidazole, Eflornithine, Melarsoprol, Nifurtimox, Oxophenarsine, Puromycin, Quinapyramine, suramin Sodium, Trypan Red, Tryparasmide ANTIPRURITIC such as Camphor, Cyproheptadine, Dichlorisone, Glycine, Halometasone, 3-Hydroxycamphor, Menthol, Mesulphen, Methdilazine, Phenol, Spirit of Camphor, Trimeprazine ANTIPSORIATIC such as Acitretin, Anthralin, 6-Azauridine, Bergapten(e), Chrysarobin, Etretinate, Pyrogallol

ANTIPSYCHOTIC

Butyrophenones such as Benperidol, Bromperidol, Droperidol, Fluanisone, Haloperidol, Melperone, Moperone, Pipamperone, Sniperone, Timiperone, Trifluperidol Phenothiazines such as Acetophenazine, Butaperazine, Carphenazine, Chlorproethazine, Chlorpromazine, Clospirazine, Cyamemazine, Dixyrazine, Fluphenazine, Imiclopazine, Mepazine, Mesoridazine, Methoxypromazine, Metofenazate, Oxaflumazine, Perazine, Pericyazine, Perimethazine, Perphenazine, Piperacetazine, Pipotiazine, Prochlorperazine, Promazine, Sulforidazine, Thiopropazate, Thioridazine, Trifluoperazine, Triflupromazine Thioxanthenes such as Chlorprothixene, Clopenthixol, Flupentixol, Thiothixene Other Tricyclics such as Benzquinamide, Carpipramine, Clocapramine, Clomacran, Clothiapine, Clozapine, Opipramol, Prothipendyl, Tetrabenazine, Zotepine Others such as Alizapride, Amisulpride, 4-Arylpiperazines, 4-Arylpiperdines, Buramate, Fluspirilene, Molindone, Penfluridol, Pimozide, Spirilene, Sulpiride ANTIPYRETIC such as Aconine, Aconite, Aconitine, Phenicarbazide ANTIRICKETTSIAL such as p-Aminobenzoic Acid ANTISEBORRHEIC such as 3-O-Lauroylpyridoxol Diacetate, Piroctone, Resorcinol, Selenium Sulfides, Tioxolone

ANTISEPTIC

Guanidines such as Alexidine, Ambazone, Chlorhexidine, Picloxydine

Halogens/Halogen Compounds such as Bornyl Chloride, Calcium Iodate, Iodine, Iodine Monochloride, Iodine Trichloride, Iodoform, Povidone-Iodine, Sodium Hypochlorite, Sodium Iodate, Symclosene, Thymol Iodide, Triclocarban, Triclosan, Troclosene Potassium Nitrofurans such as Furazolidone, 2-(Methoxymethyl)-5-Nitrofuran, Nidroxyzone, Nifuroxime, Nifurzide, Nitrofurazone Phenols such as Acetomeroctol, Chloroxylenol, Hexachlorophene, 1-Napthyl Salicylate, 2,4,6-Tribromo-m-cresol, 3',4',5-Trichlorosalicylanilide Quinolines such as Aminoquinuride, Chloroxine, Chlorquinaldol, Cloxyquin, Ethylhydrocupreine, Halquinol, Hydrastine, 8-Hydroxyquinoline Sulfate Others such as Boric Acid, Chloroazodin, m-Cresyl Acetate, Cupric Sulfate, Ichthammol ANTISPASMODIC such as Alibendol, Ambucetamide, Aminopromazine, Bietamiverine, Butaverine, Butropium, Caroverine, Cimetropium, Cinnamedrine, Clebopride, Coniine Hydrobromide, Coniine, Difemerine, Diisopromine, Dioxaphetyl Butyrate, Drofenine, Ethaverine, Fecleminee, Fenalamide, Fenoverine, Fenpiprane, Flavoxate, Flopropione, Gluconic Acid, Guaiactamine, Hydramitrazine, Hymecromone, Leiopyrrole, Mebeverine, Moxaverine, Nafiverine, Octaverine, Phenamacide, Phloroglucinol, Pinaverium, Piperilate, Pipoxolan Hydrochloride, Pramiverin, Properidine, Propivane, Propyromazine, Prozapine, Racefemine, Rociverine, Spasmolytol, Stilonium, Tiropramide, Trepibutone, Tricromyl, Trifolium, Trimebutine, N,N-1Trimethyl-3,3-diphenylpropylamine ANTITHROMBOTIC such as Anagrelide, Argatroban, Cilostazol, Daltroban, Defibrotide, Enoxaparin, Fraxiparine ®, Indobufen, Lamoparan, Ozagrel, Picotamide, Plafibride, Tedelparin, Ticlopidine, Triflusal ANTITUSSIVE such as Allocamide, Amicibone, Benproperine, Benzonatate, Bibenzonium, Bromoform, Butamirate, Butethamate, Caramiphen Ethanedisulfonate, Carbetapentane, Chlophedianol, Clobutinol, Cloperastine, Codeine Methyl Bromide, Codeine N-Oxide, Codeine Phosphate, Codeine Sulfate, Cyclexanone, Dextromethorphan, Dibunate Sodium, Dihydrocodeine, Dihydrocodeinone Enol Acetate, Dimemorfan, Dimethoxanate, $\alpha,\alpha$-Diphenyl-2-piperidinepropanol, Dropropizine, Drotebanol, Eprazinone, Ethyl Dibunate, Ethylmorphine, Fominoben, Guiaiapate, Hydrocodone, Isoaminile, Levopropoxyphene, Morclofone, Narceine, Normethadone, Noscapine, Oxeladin, Oxolamine, Pholcodine, Picoperine, Pipazethate, Piperidione, Prenoxdiazine, Racemethorphan, Taziprinone Hydrochloride, Tipepidine, Zipeprol ANTIULCERATIVE such as Aceglutamide Aluminum Complex, ε-Acetamidocaproic Acid Zinc Salt, Acetoxolone, Arbaprostil, Benexate Hydrochloride, Bismuth Subcitrate Sol (Dried), Carbenoxolone, Cetraxate, Cimetidine, Enprostil, Esaprazole, Famotidine, Ftaxilide, Gefarnate, Guaiazulene, Irsogladine, Nizatidine, Omeprazole, Ornoprostil, γ-Oryzanol, Pifarnine, Pirenzepine, Plaunotol, Ranitidine, Rioprostil, Rosaprostol, Rotraxate, Roxatidine Acetate, Sofaicone, Spizofurone, Sucralfate, Teprenone, Trimoprostil, Thrithiozine, Troxipide, Zolimidine ANTIUROLITHIC such as Acetohydroxamic Acid, Allopurinol, Potassium Citrate, Succinimide ANTIVENIN such as Lyovac ® Antivenin

ANTIVIRAL

Purines/Pyrimidinones such as 2-Acetyl-pyridine 5-((2-pyridylamino)thiocarbonyl) Thiocarbonohydrazone, Acyclovir, Dideoxyadenosine, Dideoxycytidine, Dideoxyinosine, Edoxudine, Floxuridine, Ganciclovir, Idoxuridine, MADU, Pyridinone, Trifluridine, Vidrarbine, Zidovudiine Others such as Acetylleucine Monoethanolamine, Acridinamine, Alkylisooxazoles, Amantadine, Amidinomycin, Cuminaldehyde Thiosemicarbzone, Foscarnet Sodium, Kethoxal, Lysozyme, Methisazone, Moroxydine, Podophyllotoxin, Ribavirin, Rimantadine, Stallimycin, Statolon, Thymosins, Tromantadine, Xenazoic Acid

ANXIOLYTIC

Arylpiperazines such as Buspirone, Gepirone, Ipsapirone

Benzodiazepine Derivatives Alprazolam, Bromazepam, Camazepam, Chlordiazepoxide, Clobazam, Clorazepate, Chotiazepam, Cloxazolam, Diazepam, Ethyl Loflazepate, Etizolam, Fluidazepam, Flutazolam, Flutoprazepam, Halazepam, Ketazolam, Lorazepam, Loxapine, Medazepam, Metaclazepam, Mexazolam, Nordazepam, Oxazepam, Oxazolam, Pinazepam, Prazepam, Tofisopam Carbamates such as Cyclarbamate, Emylcamate, Hydroxyphenamate, Meprobamate, Phenprobamate, Tybamate Others Alpidem, Benzoctamine, Captodiamine, Chlormezanone, Etifoxine, Fluoresone, Glutamic Acid, Hydroxyzine, Mecloralurea, Mephenoxalone, Oxanamide, Phenaglycodol, Suriclone BENZODIAZEPINE ANTAGONIST such as Flumazenil

BRONCHODILATOR

Ephedrine Derivatives such as Albuterol, Bambuterol, Bitolterol, Carbuterol, Clenbuterol, Clorprenaline, Dioxethedrine, Eprozinol, Etafedrine, Ethylnorepinephrine, Fenoterol, Hexoprenaline, Isoetharine, Isoproterenol, Mabuterol, Metaproterenol, N-Methylephedrine, Pirbuterol, Procaterol, Protokylol, Reproterol, Rimiterol, Soterenol, Terbutaline, Tulobuterol Quaternary Ammonium Compounds such as Clutropium Bromide, Oxitropium Bromide Xanthine Derivatives such as Acefylline, Acefylline Ambuphylline, Aminophylline, Bamifylline, Choline Theophyllinate, Doxofylline, Dyphylline, Enprofylline, Etamiphyllin, Etofylline, Guaithylline, Proxyphylline, Theobromine, 1-Theobromineacetic Acid, Theophylline Others such as Methoxyphenanime, Tretoquinol

CALCIUM CHANNEL BLOCKER

Arylalkylamines such as Bepridil, Ditiazem, Fendiline, Gallopamil, Terodiline, Verapamil Dihydropyridine Derivatives such as Felodipine, Isradipine, Nicardipine, Nifedipine, Nilvadipine, Nimodipine, Nisoldipine, Nitrendipine Piperazine Derivatives such as Flunarisine Others such as Perhexiline CALCIUM REGULATOR such as Calcifediol, Calcitonin, Calcitriol, Clodronic Acid, Dihydrotachysterol, Elcatonin, Etidronic Acid, Ipriflavone, Pamidronic Acid, Parathyroid Hormone, Teriparatide Acetate CARDIOTONIC such as Acetyldigititoxins, 2-Amino-4-picoline, Amrinone, Buclasdesine, Cerberoside, Camphotamide, Convallatoxin, Cymarin, Denopamine, Deslanoside, Ditalin, Digitalis, Digitoxin, , Digoxin, Dobutamine, Dopamine, Dopexamine, Enoximone, Erythrophleine, Fenalcomine, Gitalin, Gitoxin, Glycocyamine, Heptaminol, Hydrastinine, Lanotodises, Metamivam, substituted Methoxyphenyl-4,5-dihydro-3(2H)-pridazinones, Milrinone, Neriifolin, Oleandrin, Ouabain, Oxyfedrine, Prenalterol, Proscillaridin, Resibufogenin, Scillaren, Scillarenin, Strophanthin, Sulmazole, Theobromine, Xamoterol CHELATING AGENT such as Deferozmine, Edetate Calcium Disodium, Edetate Disodium, Edeate Sodium, Edetate Trisodium, Pentetate Calcium Trisodium, Pentectic Acid, Succimer, Trientine CHOLECYSTOKININ ANTAGONIST (CCK Antagonist)

CHOLELITHOLYTIC AGENT such as Chenodiol, Methyl tert-Butyl Ether, Monooctanoin, Ursodiol CHOLERETIC such as Alibendol, Anethole Trithion, Azintamide, Cholic Acid, Cicrotoic Acid, Clanobutin, Cyclobutyrol, Cyclovalone, Cynarin(e), Dehydrocholic Acid, Deoxycholic Acid, Dimecrotic Acid, α-Ethylbenzyl Alcohol, Exiproben, Feguprol, Fencibutirol, Fenipentol, Florantyrone, Hymecromone, Menbutone, 3-(o-Methoxyphenyl)-2-phenylacrylic Acid, Metochalcone, Moquizone, Osalmid, Ox Bile Extract, 4,4'-Oxydi-2-butanol, Piprozolin, Prozapine, 4-Salicyloylmorpholine, Sincalide, Taurocholic Acid, Timonacic, Tocamphyl, Trepibutone, Vanitiolide CHOLINERGIC such as Aceclidine, Acetylcholine, Acetylcholide, Aclatonium Napadisilate, Benzpyrinium Bromide, Bethanechol, Carbachol, Carpronium, Demecarium, Dexpanthenol, Diisopropyl Paraoxon, Echothiophate, Edrophomium, Eseridine, Furtrethonium, Isoflurophate, Methacholine Chloride, Muscarine, Neostigmine, Oxapropanium, Physostigmine, Pyridostigmine CHOLINESTERASE INHIBITOR such as Ambenonium, Distigmine, Galanthamine CHOLINESTERASE REACTIVATOR such as Obidoximine, Pralidoxime CNS STIMULANT/AGENT such as Amineptine, Amphetimine, Amphetaminil, Bemegride, Benzphetamine, Brucine, Caffeine, Chlorphentermine, Clofenciclan, Clortermine, Coca, Demanyl Phosphate, Dexoxadrol, Dextroamphetamine Sulfate, Diethlpropion, N-Ethylamphetamine, Ethamivan, Etifelmin, Etryptamine, Fencamfamine, Fenethylline, Fenosolone, Flurothyl, Hexacyclonate Sodium, Homocamfin, Mazindol, Megexamide, Methamphetamine, Methylphenidate, Nicotine, Nicotinic Agonist, Nikethamide, Pemoline, Pentylenetetrazole, Phenidimetrazine, Phenmetrazine, Phentermine, Picrotoxin, Pipradrol, Prolintane, Pyrovalerone, Tetrahydrobenzothienopyridines DECONGESTANT such as Cafaminol, Nordefrin DENTAL CARRIES PROPHYLACTIC such as Sodium Fluoride DEPIGMENTOR such as Hydroquinine, Hydroquinone, Monobenzone

DIURETIC

Organomercurials such as Chlormerodrin, Meralluride, Mercamphamide, Mercaptomerin Sodium, Mercumallylic Acid, Mercumatilin Sodium, Mercurous Chloride, Mersalyl Pteridines such as Furterene, Triamterene Purines such as 7-Morpholinomethyltheophylline, Pamabrom, Protheobromine, Theobromine Steroids such as Canrenone, Oleandrin, Spironolactone Sulfonamide Derivatives such as Acetazolmide, Azosemide, Bumetanide, Butazolamide, Chloraminophenamide, Clofenamide, Clorexolene, Diphenylmethane-4,4'-disulfonamide, Disulfamide, Ethoxzolamide, Flumethiazide, Mefruside, Methazolamide, Piretanide, Torasemide Uracils such as Aminometradine, Amisometradine Others such as Amanozine, Amiloride, Arbutin, Chlorazanil, Ethacrynic Acid, Etozolin, Isosorbide, Mannitol, Metochalcone, Perhexiline, Urea DOPAMINE RECEPTOR AGONIST such as Bromocriptine, Fenoldopam, Lisuride, Naxagolide, Pergolide ECTOPARASITICIDE such as Amitraz, Benzyl Benzoate, Carbaryl, Crotamiton, DDT, Dixanthogen, Isobornyl Thiocyanoacetate (Technical), Lime Sulfurated Solution, Lindane, Malathion, Mercuric Oleate, Sulphur (Pharmaceutical)

ENZYME

Digestive such as α-Amylase (Swine Pancreas), Lipase, Pancrelipase, Pepsin, Rennin Penicillin Inactivating such as Penicillinase Proteolytic such as Collagenase, Chymopapain, Chymotrypsins, Papain, Trypsin ENZYME INDUCER (HEPATIC) such as Flumecinol

ESTROGEN

Nonsteroidal such as Benzestrol, Broparoestrol, Chlorotrianisene, Dienestrol, Diethylstilbestrol, Diethylstilbestrol Diproprionate, Dimestrol, Fosfestrol, Hexestrol, Methallenestril, Methestrol Steroidal such as Colpormon, Conjugated Estrogenic Hormones, Equilenin, Equilin, Esterified Estrogens, Esteropipate, 17β-Estradiol, Estradiol, Estradiol Benzoate, Estradiol 17β-Cypionate, Estriol, Estrone, Ethinyl Estradiol, Mestranol, Moxestrol, Mytatrienediol, Polyestradiol Phosphate, Quinestradiol, Quinestrol GASTRIC SECRETION INHIBITOR such as Enterogastrone, Octreotide GLUCOCORTICOID such as 21-Acetoxyprefnenolone, Aalclometasone, Algestone, Amicinonide, Beclomethasone, Betamethasone, Betamethasone Dipropionate, Budesonide, Chloroprednisone, Clobetasol, Blovetasone, Clocortolone, Cloprednol, Corticosterone, Cortisone, Cortivazol, Deflazacort, Desonide, Desoximetasone, Dexamethasone, Diflorasone, Diflucortolone, Difluprednate, Enoxolone, Fluazacort, Flucloronide, Flumehtasone, Flunisolide, Fluocinolone Acetonide, Fluocinonide, Fluocortin Butyl, Fluocortolone, Fluorometholone, Fluperolone Acetate, Fluprednidene Acetate, Fluprednisolone, Flurandrenolide, Formocortal, Halcinonide, Halometasone, Halopredone Acetate, Hydrocortamate, Hydrocortisone, Hydrocortisone Acetate, Hydrocortisone Phosphate, Hydrocortisone 21-Sodium Succinate, Hydrocortisone Tebutate, Mazipredone, Medrysone, Meprednisone, Methyolprednisolone, Mometasone Furcate, Paramethasone, Prednicarbate, Prednisolone, Prednisolone 21-Diethylaminoacetate, Prednisone Sodium Phosphate, Prednisolone Sodium Succinate, Prednisolone Sodium 21-m-Sulfobenzoate, Prednisolone 21-Stearoylglycolate, Prednisolone Tebutate, Prednisolone 21-Trimethylacetate, Prednisone, Prednival, Prednylidene, Prednylidene 21-Diethylaminoacetate, Tixocortal, Triamcinolone, Triamcinolone Acetonide, Triamcinolone Benetonide, Triamcinolone Hexacetonide GONAD-STIMULATING PRINCIPLE such as Clomiphene, Cyclofenil, Epimestrol, FSH, HCG, LH-RH GONADOTROPIC HORMONE such as LH, PMSG GROWTH HORMONE INHIBITOR such as Somatostatin GROWTH HORMONE RELEASING FACTOR such as Semorelin GROWTH STIMULANT such as Somatotropin HEMOLYTIC such as Phenylhydrazine HEPARIN ANTAGONIST such as Hexadimethrine, Protamines HEPATOPROTECTANT such as Betaine, Citolone, Malotilate, Orazamide, Phosphorylcholine, Protoporphyrin IX, Silymarin-Group, Thiotic Acid IMMUNOMODULATOR such as Amiprilose, Bucillamine, Ditiocarb Sodium, Inosine Pranobex, Muroctasin, Platonin, Procodazole, Tetramisole, 6-aryl-5,6-dihydroimidazol-(2,1-B) Thiazole Derivatives, Thymomodulin, Thymopentin IMMUNOSUPPRESSANT such as Cyclophilin, Cyclosporins, FK-506, Mizoribine, Rapamycin, Rapamycin Sulfamates ION EXCHANGE RESIN such as Carbacrylic Resins, Resodec, Sodium Polystyrene Sulfonate LACTATION STIMULATING HORMONE such as Prolactin LH-RH AGONIST such as Buserelin, Goserelin, Leuprolide, Nafarelin, Triptorelin LIPOTROPIC such as N-Acetylmethionine, Choline Chloride, Choline Dehydrocholate, Choline Dihydrogen Citrate, Inositol, Lecithin, Methionine LUPUS ERYTHEMATOSUS SUPPRESSANT such as Bismuth Sodium Triglycollamate, Bismuth Subsalicylate MINERALOCORTICOID such as Aldosterone, Deoxycorticosterone, Fludrocortisone MIOTIC such as Pilocarpus MONOAMINE OXIDASE INHIBITOR such as Phenoxypropazine, Pivalylbenzhydrazine MUCOLYTIC such as Acetylcysteine, Bromhexine, Carbocysteine, Domiodol, Letosteine, Mecysteine, Mesna, Sobrerol, Stepronin, Tiopronin, Tyloxapol MUSCLE RELAXANT (SKELETAL) such as Afloqualone, Alcuronium, Atracurium Besylate, Baclofen, Benzoquinonium, C-Calebassine, Carisoprodol, Chlorphenesin Carbamate, Chlozoxazone, Curare, Cyclobenzaprine, Dantrolene, Decamethonium, Eperisone, Fazadinium, Flumetramide, Gallamine Triethiodide, Hexacarbacholine, Hexafluorenium, Idrocilamide, Lauexium Methyl Sulfate, Leptodactyline, Memantine, Mephenesin, Metaxalone, Methocarbamol, Metocurine Iodide, Pancuronium, Pipecurium, Promoxolane, Quinine Sulfate, Styramate, Succinylcholine, Succinylcholine Suxethonium Bromide, Tetrazepam, Thiocolchicoside, Tizanidine, Tolperisone, Tubocurarine, Vecuronium, Zoxolamine NARCOTIC ANTAGONIST such as Amiphenazole, Cyclazocine, Levallorphan, Nadide, Nalmafene, Nalorphine, Nalorphine Dinicotinate, Naloxone, Naltrexone NEUROPROTECTIVE such as Dizocilpine NOOTROPIC such as Aceglutamide, Acetylcarnitine, Aniracetam, Bifematlane, Exifone, Fipexide, Idebenone, Indeloxazune, Nizofenone, Oxiracetam, Piracetam, Propentofylline, Pyritinol OPHTHALMIC AGENT such as 15-ketoprostaglandins OVARIAN HORMONE such as Relaxin OXYTOCIC such as Carboprost, Cargutocin, Deaminooxytocin, Ergonovine, Gemeprost, Methylergonovine, Oxytocin, Pituitary (Posterior), Prostaglandin $E_2$, Prostaglandin $F_{2\alpha}$, Sparteine PEPSIN INIBITOR such as Sodium Amylosulfate PERISTALTIC STIMULANT such as Cisapride PROGESTOGEN such as Allylestrenol, Anagestone, Chlormadinone Acetate, Delmadinone Acetate, Demegestone, Desogestrel, Dimethisterone, Dydrogesterone, Ethinylestrenol, Ethisterone, Ethynodiol, Ethynodiol Diacetate, Flurogestone Acetate, Gestodene, Gestonorone Caproate, Haloprogesterone, 17-Hydroxy-16-methylene-progesterone, 17α-Hydroxyprogesterone, 17α-Hydroxygesterone Caproate, Lynestrenol, Medrogestone, Medroxyprogesterone, Megestrol Acetate, Melengestrol, Norethindrone, Norethindrone Acetate, Norethynodrel, Norgesterone, Norgestimate, Norgestrel, Norgestrienone, 19-Norprogesterone, Norvinisterone, Pentagestrone, Progesterone, Promegestone, Quingestrone, Trengestone PROLACTIN INHIBITOR such as Metergoline PROSTAGLANDIN/PROSTAGLANDIN ANALOG such as Bemeprost, Prostacyclin, Prostaglandin $E_1$, Sulprostone PROTEASE INHIBITOR such as Aprotinin, Camostat, Gabexate, Nafamostat RESPIRATORY STIMULANT such as Almitrine, Dimefline, Dimorpholamine, Doxapram, Lobeline, Mepixanox, Pimeclone, Sodium Succinate, Tacrine SCLEROSING AGENT such as Ethanolamine, Ethylamine, 2-Hexyldecanoic Acid, Sodium Ricinoleate, Sodium Tetradecyl Sulfate, Tribenoside

SEDATIVE/HYPNOTIC

Acyclic Ureides such as Acecarbromal, Apronalide, Bomisovalum, Capuride, Carbromal, Ectylurea Alcohols such as Chlorhexadol, Ethchlorvynol, 4-Methyl-5-thiazoleethanol, tert-Pentyl Alcohol, 2,2,2-Trichloroethanol Amides such as Butoctamide, Diethylbromoacetamide, Ibrotamide, Isovaleryl Diethylamide, Niaprazine, Tricetamide, Trimetozine, Zolpidem, Zopiclone Barbituric Acid Derivatives such as Allobarbital, Amobarbital, Aprobarbital, Barbital, Brallabarbital, Butabarbital Sodium, Butalbital, Butallylonal, Butethal, Carbubarb, Cyclobarbital, Cyclopentobarbital, Enallylpropymal, 5-Ethyl-5-(1-piperidyl) barbituric Acid, 5-Furfuryl-5-isopropylbarbituric Acid, Heptabarbital, Hexethal Sodium, Hexobarbital, Mephobarbital, Methitural, Narcobarbital, Nealbarbital, Pentobarbital Sodium, Phenallymal, Phenobarbital, Phenobarbital Sodium, Phenylmethylbarbituric Acid, Probarbital, Propallylonal, Proxibarbal, Reposal, Secobarbital Sodium, Talbutal, Tetrabarbital, Vinbarbital Sodium, Vinylbital Benzodiazepine Derivatives such as Brotizolam, Doxefazepam, Estazolam, Flunitrazepam, Flurazepam, Haloxazolam, Loprazolam, Lormetazepam, Nitrazepam, Quazepam, Temasepam, Triazolam Bromides such as Ammonium Bromide, Calcium Bromide, Calcium Bromolactobionate, Lithium Bromide, Magnesium Bromide, Potassium Bromide, Sodium Bromide Carbamates such as Amyl Carbamate (Tertiary), Ethinamate, Hexaprpymate, Meparfynol Carbamate, Novonal, Tricholorourethan Chloral Derivatives such as Carbocloral, Chloral Betaine, Chloral Formamide, Chloral Hydrate, Chloralantipyrine, Dichloralphenazone, Pentaerythritol Chloral, Triclofos Piperidinediones such as Glutehimide, Methyprylon, Piperidione, Pyrithyldione, Taglutimide, Thalidomide Quinazolone Derivatives such as Etaqualone, Mecloqualone, Methaqualone Others such as Acetal, Acetophenone, Aldol, Ammonium Valerate, Amphenidone, d-Bornyl α-Bromoisovalerate, d-Bornyl Isovalerate, Bromoform, Calcium 2-Ethylbutanoate, Carfinate, α-Chlorolose, Clomethiazole, Cypripedium, Doxylamine, Etodroxizine, Etomidate, Fenadiazole, Homofenazine, Hydrobromic Acid, Mecloxamine, Menthyl Valerate, Opium, Paraldehyde, Perlapine, Propiomazine, Rilmazafone, Sodium Oxybate, Sulfonethylmethane, Sulfonmethane THROMBOLYTIC such as APSAC, Plasmin, Pro-Urokinase, Streptokinase, Tissue Plasminogen Activator, Urokinase THYROTROPIC HORMONE such as TRH, TSH URICOSURIC such as Benzbromarone, Ethebenecid, Orotic Acid, Zoxazolamine VASODILATOR (CEREBRAL) such as Bencyclane, Ciclonicate, Cinnarizine, Citicoline, Diisopropylamine Dichloractetate, Eburnamonine, Fenoxedil, Ibudilast, Ifenprodil, Nafronyl, Nicametate, Nicergoline, Nimodipine, Papaverine, Pentifylline, Tinofedrine, Vincamine, Vinpocetine VASODILATOR (CORONARY) such as Amotriphene, Bendazol, Benfurodil Hemisuccinate, Benziodcarone, Chloacizine, Chromonar, Clobenfurol, Clonitrate, Dilazep, Dipyridamole, Droprenilamine, Efloxate, Erythritol, Erythrityl Tetranitrate, Etafenone, Floredil, Ganglefene, Hexestrol Bis($\beta$-diethylaminoethyl ether), Hexobendine, Isosorbitol Dinitrate, Itramin Tosylate, Khellin, Lidoflazine, Mannitol Hexanitrate, Medibazine, Nicorandil, Nitroglycerin, Pentaerythritol Tetranitrate, Pentrinitrol, Pimefylline, Potassium Nitrite, Prenylamine, Propatyl Nitrate, Pyridofylline, Trapidil, Tricromyl, Trimetazidine, Trolnitrate Phosphate, Visnadine VASODILATOR (PERIPHERAL) such as Bamethan, Betahistine, Bradykinin, Brovincamine, Bufoniode, Buflomedil, Butalamine, Cetiedil, Ciclonicate, Cinepazide, Cyclandelate, Eledoisin, Heronicate, Inositol Niacinate, Isoxsuprine, Kallidin, Kallikrein, Moxisylyte, Nicofuranose, Nicotinyl Alcohol, Nylidrin, pentoxifylline, Piribedil, Suloctidil, Xanthinal Niacinate VASOPROTECTANT such as Benzarone, Bioflavonoids, Chromocarb, Clobeoside, Diosmin, Dobesilate Calcium, Escin, Rolescutol, Leucocyanidin, Metescufylline, Quercetin, Rutin, Troxerutin VITAMIN/VITAMIN SOURCE/EXTRACTS such as Vitamins A, B, C, D, E, and K and derivatives thereof, Calciferols, Glycyrrhiza, Mecobalamin VULNERARY such as Allantoin, Asiaticoside, Cadexomer Iodine, Chitin, Dextranomer The above list of pharmaceutical agents is based upon the list provided in The Merk Index, 11th Edition, Merck & Co. Rahway, N.J. (1989). Moreover, the above drugs may be used either in the free form or, if capable of forming salts, in the form of a saly with a suitable acid or base; if the drug has a carboxyl group, its esters may also be employed.

What is claimed is:

1. A flexible, finite, bioadhesive composition for topical application comprising:
   (a) a therapeutically effective amount of at least one pharmaceutically active agent which is in solid form at ambient temperatures and pressures;
   (b) a pharmaceutically acceptable solvent for the pharmaceutically active agent, in an amount from about 5 to about 70 weight percent based on the weight of the whole composition, said solvent including about 5 to about 50 weight percent of a plasticizer;
   (c) in admixture with the pharmaceutically active agent in the solvent, a pharmaceutically acceptable polysaccharide bioadhesive carrier in an amount from about 20 to about 50 weight percent based on the weight of the whole composition;
   wherein the composition is substantially free of water, substantially water insoluble and is a bioadhesive; and wherein the pharmaceutically active agent is present in non-crystallized form in the composition.

2. The composition of claim 1, wherein the pharmaceutically acceptable solvent is in an amount from about 20 to about 53 weight percent based on the weight of the whole composition, of which the plasticizer represents about 10 to about 30 weight percent based on the weight of the whole composition, and the bioadhesive carrier is in an amount from about 20 to about 34 weight percent based on the weight of the whole composition.

3. The composition of claim 1, wherein the pharmaceutically active agent is at least one local anesthetic in an amount of about 10 to 40 weight percent based on the weight of the total composition.

4. The composition of claim 1, wherein the pharmaceutically active agent is from a class of drugs selected from the group consisting of analgesic anti-inflammatory drugs, central nervous system drugs, antihistaminic or antiallergic drugs, acitonide anti-inflammatory drugs, androgenic and estrogenic steroids, -respiratory drugs, sympathomimetic drugs, antimicrobial drugs, antihypertensive drugs, cardiotonic drugs, coronary vasodilators, vasoconstrictors, beta blocking and antiarrhythemic drugs, calcium antagonistic and other circulatory anticonvulsants, anti-vertigo-tranquilizing drugs, antipsychotic drugs, muscle-reactants drugs, anti-Parkinson drugs, non-steroidal hormones, anti-hormones, vitamins, antitumor, enzymes, herb medicines or crude extracts, miotics, cholinergic agonists, antimuscarinic or muscarinic cholinergic blocking drugs, mydriatics, psychic energizers, humoral agents, antispasmodic drugs, antidepressants, antidiabetics, anorexic drugs, anti-allergic drugs, decongestants, antipyretics, antimigraine drugs, antimalarial, antiulcer drugs, peptides, and anti-estrogens.

5. The composition of claim 4, in which the pharmaceutically active agent is one or more steroids selected from the group consisting of androgenic steroids, including testosterone; methyltestosterone; fluoxymesterone; estrogenic steroids, including conjugated estrogens, esterified estrogens, estropipate, 17-$\beta$ estradiol, 17-$\beta$ estradiol esters such as 17-$\beta$-estradiol valerate, equilin, mestranol, estrone, estriol; 17-$\beta$ estradiol derivatives such as 17-$\beta$ ethinyl estradiol; diethylstilbestrol, progestational agents, including progesterone and progesterone analogs such as 19norprogesterone, hydroxyprogesterone caproate, 17-$\alpha$ hydroxyprogesterone, dydrogesterone, medroxyprogesterone acetate; and norethindrone, norethindrone acetate, melengestrol, chlormadinone; ethynodiol diacetate, norethynodrel, dydrogesterone, dimethisterone, ethinylestrenol, norgestrel, demegestone, promegestone, megestrol acetate, and anti-estrogen or anti-androgenic steroids.

6. The composition of claim 3, wherein the anesthetic agent is selected from the group consisting of procaine, lidocaine, prilocaine, mepivacaine, dyclonine, dibucaine, benzocaine, chloroprocaine, tetracaine, bupivacaine, and etidocaine and is in the form of the base or an acid-addition salt or both forms.

7. The composition of claim 6, wherein the acid-addition salt is hydrochloride.

8. The composition of claim 1, wherein the bioadhesive is selected from the group consisting of gums and celluloses.

9. The composition of claim 8, wherein the gum is selected from the group consisting of karaya gum, tragacanth gum, pectin gum, xanthan gum, guar gum, cellulose, and cellulose derivatives.

10. The composition of claim 3, wherein the solvent for the anesthetic agent is at least one polyhydric alcohol.

11. The composition of claim 10, wherein the polyhydric alcohol is a polyalkylene glycol.

12. The composition of claim 11, wherein the glycol is selected from the group consisting of dipropylene glycol, propylene glycol, ethylene glycol, polyethylene glycol, glycerin, butylene glycol, hexylene glycol, polypropylene glycol, and sorbitol.

13. The composition of claim 1 further comprising a backing material conforming to the size and shape of a single dosage of the composition.

14. The composition of claim 1 comprising about 20 to 34 weight percent of karaya gum, about 20 to 53 weight percent of at least one glycol, and about 10 to 25 weight percent of lidocaine base
and further comprising a binder in an amount sufficient to bind the other ingredients.

15. The composition of claim 14 comprising about 30 weight percent of karaya gum, about 6 weight percent propylene glycol, about 15 weight percent of dipropylene glycol, about 15 weight percent of glycerine, about 25 weight percent of lidocaine base and about 9 weight percent of lecithin.

16. The composition of claim 14, comprising about 33 weight percent of karaya gum, about 7 weight percent of propylene glycol, about 12 weight percent of dipropylene glycol, weight percent of glycerin, about 10 weight percent lidocaine base and about 5 weight percent lecithin.

17. The composition of claim 1, wherein the pharmaceutically active agent is an anti-microbial agent.

18. The composition of claim 17, wherein the antimicrobial agent in an antifungal agent.

19. The composition of claim 18, wherein the antimicrobial agent is clotrimazole.

20. The composition of claim 18, wherein the antimicrobial agent is miconazole.

21. A method of administering one or more pharmaceutically active agent to a subject comprising the steps of:
providing the composition set forth in claim 1; and
contacting an area of skin or mucous membrane with the composition to administer the pharmaceutically active agent.

22. The method of claim 21, wherein the pharmaceutically active agent is an anesthetic agent selected from the group consisting of procaine, dyclonine, lidocaine, prilocaine, mepivacaine, benzocaine, propoxycaine, chloroprocaine, tetracaine, bupivacaine, etidocaine, and dibucaine.

23. The method of claim 22, wherein the anesthetic agent is administered in the form of a free base.

24. The method of claim 22, wherein the anesthetic agent is administered in the form of an acid-addition salt.

25. The method of claim 22, wherein the solvent is at least one polyhydric alcohol.

26. A composition for topical application comprising:
(a) a therapeutically effective amount of a first local anesthetic agent in base form;
(b) a therapeutically effective amount of a different, second local anesthetic agent in non-salicylate acid-addition salt form; and
(c) in an admixture with the anesthetic agents, a pharmaceutically acceptable carrier wherein the anesthetic agents comprise about 1 to about 50% by weight of the total composition.

27. The composition of claim 26, wherein the first local anesthetic agent in base form is selected from the group consisting of procaine, dyclonine, lidocaine, prilocaine, mepivacaine, benzocaine, propoxycaine and chloroprocaine.

28. The composition of claim 26, wherein the second local anesthetic agent in non-salicylate acid-addition salt form is selected from the group consisting of a dyclonine salt, a prilocaine salt, a tetracaine salt, a bupivacaine salt, a mepivacaine salt, a lidocaine salt, a procaine salt, an etidocaine salt, and a dibucaine salt.

29. The composition of claim 26, wherein the first local anesthetic agent in base form is selected from the group consisting of procaine, dyclonine, lidocaine, prilocaine, mepivacaine, benzocaine, propoxycaine and chloroprocaine and the -second local anesthetic in acid-addition salt form is selected from the group consisting of a dyclonine salt, a prilocaine salt, a tetracaine salt, a bupivacaine salt, a mepivacaine salt, a lidocaine salt, a procaine salt, an etidocaine salt, and a dibucaine salt.

30. The composition of claim 29, wherein the acid addition salt is the hydrochloride.

31. A composition for topical application comprising:
(a) a therapeutically effective amount of a first local anesthetic agent in base form;
(b) a therapeutically effective amount of a different, second local anesthetic agent in acid-addition salt form; and
(c) in an admixture with the anesthetic agents, a pharmaceutically acceptable carrier which is substantially free of water
wherein the anesthetic agents comprise about 1 to about 50% by weight of the total composition and wherein said composition is substantially free of water.

32. The composition of claim 31, wherein the first local anesthetic agent in base form is selected from the group consisting of procaine, dyclonine, lidocaine, prilocaine, mepivacaine, benzocaine, propoxycaine and chloroprocaine.

33. The composition of claim 31, wherein the second local anesthetic agent in acid-addition salt form is selected from the group consisting of a dyclonine salt, a prilocaine salt, a tetracaine salt, a bupivacaine salt, a mepivacaine salt, a lidocaine salt, a procaine salt, an etidocaine salt, and a dibucaine salt.

34. The composition of claim 33, wherein the first local anesthetic agent in base form is selected from the group consisting of procaine, dyclonin, lidocaine, prilocaine, mepivacaine, benzocaine, propoxycaine and chloroprocaine and the second local anesthetic in acid-addition salt form is selected from the group consisting of a dyclonine salt, a prilocaine salt, a tetracaine salt, a bupivacaine salt, a mepivacaine salt, a lidocaine salt, a procaine salt, an etidocaine salt, and a dibucaine salt.

35. The composition of claim 34, wherein the acid addition salt is the hydrochloride.

36. The composition of claim 26 or 31, wherein the solvent for the anesthetic agent is at least one polyhydric alcohol.

37. The composition of claim 36, wherein the polyhydric alcohol is a polyalkylene glycol.

38. The composition of claim 37, wherein the glycol is selected from the group consisting of dipropylene glycol, propylene glycol, ethylene glycol, polyethylene glycol, glycerin, butylene glycol, hexylene glycol, polypropylene glycol, and sorbitol.

39. The composition of claim 26 or 31, further comprising a backing material which conforms to the size and shape of a single dosage of the composition.

40. The method of administering the composition of claim 26 to a subject, comprising the steps of:
   (a) providing a composition set forth in claim 26; and
   (b) contacting an area of tissue with the composition to administer the local anesthetics.

41. The method of claim 40, wherein the first local anesthetic agent in base form is selected from the group consisting of procaine, dyclonine, lidocaine, prilocaine, mepivacaine, benzocaine, propoxycaine and chloroprocaine and the second local anesthetic agent in acid-addition salt form is selected from the group consisting of a dyclonine salt, a prilocaine salt, a tetracaine salt, a bupivacaine salt, a mepivacaine salt, a lidocaine salt, a procaine salt, an etidocaine salt, and a dibucaine salt.

42. The method of claim 41, wherein the acid-addition salt is hydrochloride.

43. The method of administering the composition of claim 31 to a subject, comprising the steps of:
   (a) providing a composition set forth in claim 31; and
   (b) contacting an area of tissue with the composition to administer the local anesthetics.

44. The method of claim 43, wherein the first local anesthetic agent in base form is selected from the group consisting of procaine, dyclonine, lidocaine, prilocaine, mepivacaine, benzocaine, propoxycaine and chloroprocaine and the second local anesthetic agent in acid-addition salt form is selected from the group consisting of a dyclonine salt, a prilocaine salt, a tetracaine salt, a bupivacaine salt, a mepivacaine salt, a lidocaine salt, a procaine salt, an etidocaine salt, and a dibucaine salt.

45. The method of claim 43, wherein the acid-addition salt is hydrochloride.

* * * * *

UNITED STATES PATENT AND TRADEMARK OFFICE
CERTIFICATE OF CORRECTION

PATENT NO. : 5,446,070
DATED : August 29, 1995
INVENTOR(S) : Juan A. MANTELLE

It is certified that error appears in the above-indentified patent and that said Letters Patent is hereby corrected as shown below:

On the Cover page, section [73], "Nover" should read --Noven--.

Signed and Sealed this

Nineteenth Day of March, 1996

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,446,070
DATED : August 29, 1995
INVENTOR(S) : Juan A. MANTELLE

It is certified that error appears in the above-indentified patent and that said Letters Patent is hereby corrected as shown below:

column 41, line 41, "Merk" should read --Merck--; and line 44, "saly" should read --salt--.

Signed and Sealed this

Twenty-eighth Day of May, 1996

Attest:

BRUCE LEHMAN

Attesting Officer     Commissioner of Patents and Trademarks